US010874607B2

(12) United States Patent
Tan et al.

(10) Patent No.: US 10,874,607 B2
(45) Date of Patent: *Dec. 29, 2020

(54) ISOTRETINOIN ORAL-MUCOSAL FORMULATIONS AND METHODS FOR USING SAME

(71) Applicant: Skyline Biosciences LLC, Northbrook, IL (US)

(72) Inventors: Hock S. Tan, East Brunswick, NJ (US); Siew L. Chung, East Brunswick, NJ (US)

(73) Assignee: Skyline Biosciences LLC, Northbrook, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/698,063

(22) Filed: Nov. 27, 2019

(65) Prior Publication Data

US 2020/0093735 A1    Mar. 26, 2020

Related U.S. Application Data

(63) Continuation of application No. PCT/US2018/040267, filed on Jun. 29, 2018.

(60) Provisional application No. 62/526,743, filed on Jun. 29, 2017.

(51) Int. Cl.
| | |
|---|---|
| *A61K 9/00* | (2006.01) |
| *A61K 31/203* | (2006.01) |
| *A61K 47/32* | (2006.01) |
| *A61K 31/201* | (2006.01) |
| *A61K 47/10* | (2017.01) |

(52) U.S. Cl.
CPC ............ *A61K 9/006* (2013.01); *A61K 31/201* (2013.01); *A61K 31/203* (2013.01); *A61K 47/10* (2013.01); *A61K 47/32* (2013.01)

(58) Field of Classification Search
CPC .... A61K 9/006; A61K 31/201; A61K 31/203; A61K 47/10; A61K 47/32
See application file for complete search history.

(56) References Cited

U.S. PATENT DOCUMENTS

| | | | |
|---|---|---|---|
| 4,727,088 A | 2/1988 | Scott et al. | |
| 4,985,235 A * | 1/1991 | Kligman | A61K 8/671 424/49 |
| 5,188,817 A * | 2/1993 | Ozick | A61K 8/671 424/435 |
| 7,435,427 B2 | 10/2008 | Vanderbist et al. | |
| 8,241,661 B1 | 8/2012 | Fuisz et al. | |
| 8,367,102 B2 | 2/2013 | Vanderbist et al. | |
| 8,952,064 B2 | 2/2015 | Vanderbist et al. | |
| 9,078,925 B2 | 7/2015 | DeBoeck et al. | |
| 9,089,534 B2 | 7/2015 | Vanderbist et al. | |
| 2001/0018059 A1 | 8/2001 | Gehlsen | |
| 2003/0082114 A1 * | 5/2003 | Kim | A61K 8/0208 424/53 |
| 2007/0037779 A1 | 2/2007 | Curd et al. | |
| 2008/0025925 A1 * | 1/2008 | Allred | A61K 8/22 424/53 |
| 2014/0323507 A1 * | 10/2014 | Tsai | A61K 31/365 514/274 |
| 2016/0089353 A1 | 3/2016 | Rao et al. | |
| 2020/0093734 A1 | 3/2020 | Tan et al. | |

FOREIGN PATENT DOCUMENTS

| | | |
|---|---|---|
| CN | 103319365 A | 9/2013 |
| EP | 1 755 552 | * 10/2012 |
| WO | WO-2006/117803 A2 | 11/2006 |

OTHER PUBLICATIONS

Lotan, Reuben et al., The New England Journal of Medicine, vol. 332, No. 21, pp. 1405-1410 (May 25, 1995) (Year: 1995).*
MatWeb, Evonik Eudragit RL 100 Copolymer, acessed Feb. 13, 2020, pp. 1-2 (Year: 2020).*
Toma S. et al., "Progressive 13-cis-retinoic Acid Dosage in the Treatment of Oral Leukoplakia," European Journal of Cancer. Part B, Oral Oncology, Pergamon, Oxford, GB, vol. 28, No. 2, Jan. 1, 1992, pp. 121-123.
International Search Report and Written Opinion; PCT/US2018/040267; dated Sep. 13, 2018; 10 pages.
Brazzell et al. "Pharmacokinetics of the Retinoids Isotretinoin and Etretinate" Journal of the American Academy of Dermatology; vol. 6, No. 4, Apr. 1982; pp. 643-651.
Hixson et al. "Comparative Subacute Toxicity of all-trans- and 13-cis-Retinoic Acid in Swiss Mice" Toxicology and Applied Pharmacology 44, pp. 29-40 (1978).
Mukherjee et al. "Retinoids in the treatment of skin aging: an overview of clinical efficacy and safety" Clinical Interventions in Aging 2006:1(4) pp. 327-348.
Patel et al. "Improving the Isotretinoin Photostability by Incorporating in Microemulsion Matrix" International Scholarly Research Network Pharmaceutics; vol. 2011; pp. 1-6.
Petruzzi et al. "Topical Retinoids in Oral Lichen Planus Treatment: An Overview" Dermatology; 2013; pp. 1-7.

(Continued)

*Primary Examiner* — Dennis J Parad
*Assistant Examiner* — Lyndsey M Beckhardt
(74) *Attorney, Agent, or Firm* — Goodwin Procter LLP

(57) ABSTRACT

Disclosed herein, in part, is a pharmaceutical formulation comprising isotretinoin or a pharmaceutically acceptable salt thereof, and a mucoadhesive polymer. A method of treating a mucosal disease comprising administering a disclosed pharmaceutical formulation to a subject in need thereof is also provided herein.

7 Claims, 4 Drawing Sheets

(56) References Cited

OTHER PUBLICATIONS

Piattelli et al. "bcl-2 expression and apoptotic bodies in 13-cis-retinoic acid (isotretinoin)-topically treated oral leukoplakia: a pilot study" Oral Oncology 35 (1999); pp. 314-320.
Scardina et al. "A randomized trial assessing the effectiveness of different concentrations of isotretinoin in the management of lichen planus" Int. J. Oral Maxillofac. Surg. 2006; 35: pp. 67-71.
Scardina et al. "Evaluation of the Clinical and Histological Effectiveness of Isotretinoin in the Therapy of Oral Leukoplakia Ten Years of Experience: Is Management Still Up to Date Effective?" Methods Find Exp Clin Pharmacol 2006, 28(2); pp. 115-119.
Scardina et al. "Oral Leukoplakia" Dent. Med. Probl. 2005, 42, 1, pp. 37-40.
Sudhakar Y. et al. "Buccal bioadhesive drug delivery—A promising option for orally less efficient drugs", Journal of Controlled Release, Elsevier, Amsterdam, NL, vol. 114, No. 1, Aug. 10, 2006 (Aug. 10, 2006), pp. 15-40.
Tan et al. "Determination of the kinetics of degradation of 13-cis-retinoic acid and all-trans-retinoic acid in solution" Journal of Pharmaceutical & Biomedical Analysis; vol. 11, No. 9, pp. 817-822, 1993.
Tan et al. "Solid-State Stability Studies of 13-cis-Retinoic Acid and All-trans-Retinoic Acid Using Microcalorimetry and HPLC Analysis" Pharmaceutical Research, vol. 9, No. 9, 1992, pp. 1203-1208.
Tsukuda et al. "13-cis Retinoic Acid Exerts its Specific Activity on Human Sebocytes through Selective Intracellular Isomerization to All-trans Retinoic Acid and Binding to Retinoid Acid Receptors" The Journal of Investigate Dermatology; vol. 115, Aug. 2000, pp. 321-327.

* cited by examiner

ISOTRETINOIN ORAL-MUCOSAL FORMULATIONS AND METHODS FOR USING SAME

CROSS-REFERENCE TO RELATED APPLICATION

This application is a continuation of International Application No. PCT/US2018/040267, filed Jun. 29, 2018, which claims priority to and the benefit of U.S. Provisional Patent Application No. 62/526,743, filed Jun. 29, 2017, each of which are incorporated herein by reference in their entirety.

BACKGROUND

Isotretinoin is 13-cis-retinoic acid and is a derivative of vitamin A. Isotretinoin was originally developed and approved for the treatment of acne. However, it has been extensively studied for use in the treatment of various diseases, including neuroblastoma, recurrent prostate cancer, leukemia, high-grade glioma, head and neck cancers and multiple myeloma, certain dermatological disorders such as xeroderma pigmentosum, gram-negative folliculitis, recalcitrant rosacea, pyoderma faciale, generalized lichen planus, psoriasis, cutaneous lupus erythematosus, acne fulminans, and squamous cell carcinoma, as well as mucosal diseases. Isotretinoin was initially developed as a capsule, and subsequently gel and cream formulations were also developed.

Mucoadhesive films have emerged as advanced dosage forms that provide a useful alternative to traditional tablets, capsules, soft gels and liquids. Mucoadhesive films are thin film strips, squares or discs containing an active pharmaceutical ingredient (API) and typically designed for intraoral administration, with the patient placing the strip on or under the tongue (lingual or sublingual) or along the inside of the cheek (buccal). As the thin film dissolves/erodes, the drug is released and delivered into the blood stream either intragastrically, buccally or sublingually.

Mucoadhesive films can generally be classified into two categories: fast dissolving/eroding films and slow dissolving/eroding films. Fast dissolving/eroding films, which typically comprise polymers of high water solubility, are designed as a convenient form for lingual administration and gastro-intestinal (GI) tract absorption. The active ingredients are incorporated in the film matrix, which dissolves rapidly on the tongue and is then swallowed into the GI tract for absorption. No water is required, making this dosage form convenient for the consumer or patient. This type of dosage form may be particularly useful for pediatric and geriatric patients, and patients with difficulty in swallowing tablets. The second class of bioadhesive films is designed for controlled or sustained release of API. These films contain at least a slow dissolving or eroding polymer. Slow dissolving/eroding films are mainly designed for systemic administration via the interior lining of the cheek (buccal mucosa) or for local treatment.

All tablet dosage forms, soft gels and liquid formulations primarily enter the blood stream via the gastrointestinal tract, which subjects the drug to degradation from stomach acid, bile, digestive enzymes and other first pass effects. As a result, such formulations often require higher doses and generally have a delayed onset of action. Non-systemic buccal and sublingual thin film drug delivery can avoid these issues and yield quicker onsets of action at lower doses.

However, it remains a challenge to deliver an active agent buccally while minimizing systemic interaction and buccal irritation. Further, there remains a pressing need for treatment of oral premalignant lesions and other oral cavity or oropharynx disorders to assist in preventing progression to malignant lesions. Currently there are no approved pharmacologic treatments for such oral premalignant lesions (OPLs).

SUMMARY

In one aspect, provided herein is a pharmaceutically acceptable film for mucosal delivery of isotretinoin. Contemplated films include isotretinoin and mucosal adhesive polymer such as described herein. For example, a mucosal adhesive pharmaceutical film is provided that comprises: a mucoadhesive layer comprising about 0.05% to about 0.5% w/w isotretinoin or a pharmaceutically acceptable salt thereof, and a mucoadhesive, hydrophilic biocompatible polymer; and optionally an occlusive backing layer.

In some embodiments, contemplated herein is a composition having a mucoadhesive layer (e.g. a mucoadhesive hydrophilic biocompatible layer) or composition that comprises a vinylpyrrolidone-vinyl acetate co-polymer and/or a polyvinylpyrrolidone (PVP). In some embodiments, a mucoadhesive hydrophilic biocompatible polymer is selected from the group consisting of a vinylpyrrolidone-vinyl acetate co-polymer, a PVP, a carbopol, a polycarbophil, a xanthan gum, an alginate or any pharmaceutically acceptable salt thereof, a chitosan, a polyethylene oxide, a polyvinyl alcohol, a cellulose polymer, and combinations thereof. For example, provided herein is a film having a mucoadhesive layer that includes a PVP has a weight average molecular weight of about 70,000 g/mol to about 1,600,000 g/mol, or e.g., a K value of 80, 85, 90 or 95, for example 90. Contemplated films may include a vinylpyrrolidone-vinyl acetate co-polymer having a weight average molecular weight of about 45,000 g/mol to about 70,000 g/mol.

A contemplated mucoadhesive layer may include about 0.1% w/w, about 0.2% w/w, about 0.3% w/w, about 0.4% w/w, or about 0.5% w/w isotretinoin, for example, about 0.1% w/w to about 1% w/w.

In some embodiments, a mucosal adhesive pharmaceutical film includes the occlusive backing layer, wherein the occlusive backing layer is substantially free of isotretinoin. A contemplated occlusive backing layer can include one or more methacrylate co-polymers. For example, an ingestible, occlusive backing layer, if present, can include a polymer selected from the group consisting of poly(methacrylic acid-co-ethylacrylate) 1:1, poly(ethyl acrylate-co-methyl methacrylate-co-trimethylammonioethyl methacrylate chloride) 1:2:0.2 and combinations thereof.

In some embodiments, the mucoadhesive layer and/or the occlusive backing layer further comprises a plasticizer. In some embodiments, the plasticizer is propylene glycol and/or a PEG. In some embodiments, the PEG has a weight average molecular weight of about 380 g/mol to about 420 g/mol. In some embodiments, the PEG is PEG 400.

A contemplated mucoadhesive layer may further comprise at least one of: an opacifying agent, a colorant, and/or an antioxidant. In some embodiments, the opacifying agent is titanium oxide. In some embodiments, the antioxidant is butylated hydroxytoluene (BHT). In some embodiments, the mucoadhesive layer further comprises a colorant and the occlusive backing layer comprises a colorant different than that in the mucoadhesive layer.

In one aspect, provided herein is a multilayered pharmaceutical formulation comprising: (1) a first layer comprising isotretinoin or a pharmaceutically acceptable salt thereof and a mucoadhesive polymer; and (2) a second layer comprising an ingestible backing film. In some embodiments, the second layer comprises a methacrylate-based co-polymer.

For example, provided herein is a pharmaceutically acceptable film wherein more than 85% of the isotretinoin is released within 60 minutes, within 20 minutes or even within 15 minutes using a USP 3 and 7 dissolution apparatus. For example, contemplated herein is a film that may be applied to a patient's mucosal region (e.g., mouth, throat) for 15 minutes, for example daily.

In one aspect, provided herein is a mucosal adhesive pharmaceutical film comprising: a mucoadhesive layer comprising about 0.1% w/w, about 0.2% w/w or about 0.3% w/w isotretinoin or a pharmaceutically acceptable salt thereof, about 12% w/w to about 15% w/w vinylpyrrolidone-vinyl acetate copolymer, about 53% w/w to about 57% w/w PVP, about 16% w/w to about 19% w/w PEG 400 and about 4% w/w to about 6% w/w propylene glycol; and an occlusive backing layer.

In some embodiments, the occlusive backing layer comprising about 40% w/w to about 45% w/w poly(methacrylic acid-co-ethylacrylate) 1:1, about 25% w/w to about 30% w/w poly(ethyl acrylate-co-methyl methacrylate-co-trimethylammonioethyl methacrylate chloride) 1:2:0.2, about 13% w/w to about 16% w/w PEG 400 and about 4% w/w to about 6% w/w propylene glycol.

In one aspect, provided herein is a kit for suitable storage of an isotretinoin oral film comprising: a multilayered laminate pouch suitable for packaging of any one of the mucosal adhesive pharmaceutical films or pharmaceutical formulations provided herein, and any one of the mucosal adhesive pharmaceutical films or pharmaceutical formulations provided herein provided herein. In some embodiments, the multilayered laminate pouch comprises polyester and polyethylene film laminate. In some embodiments, the multilayered laminate pouch further comprises aluminum.

In one aspect, provided herein is a method of treating an oral premalignant lesion in a patient in need thereof comprising mucosally applying any of the films or compositions of any one of the provided herein to the patient, thereby administering an effective amount of the isotretinoin to the patient. In some embodiments, the oral premalignant lesion is oral leukoplakia or oral erythroplakia.

In some embodiments, mucosally applying comprises applying the mucoadhesive layer to the lesion on a mucosa of the mouth of the patient. In some embodiments, one or more lesions are treated comprising applying one or more films or compositions.

In one aspect, provided herein is a method of treating an oral premalignant lesion in a patient in need thereof comprising mucosally applying an orally adhesive film comprising about 0.1 to about 0.3 w/w of isotretinoin to the oral premalignant lesion for about 30 minutes once daily.

DETAILED DESCRIPTION

Figure 1:
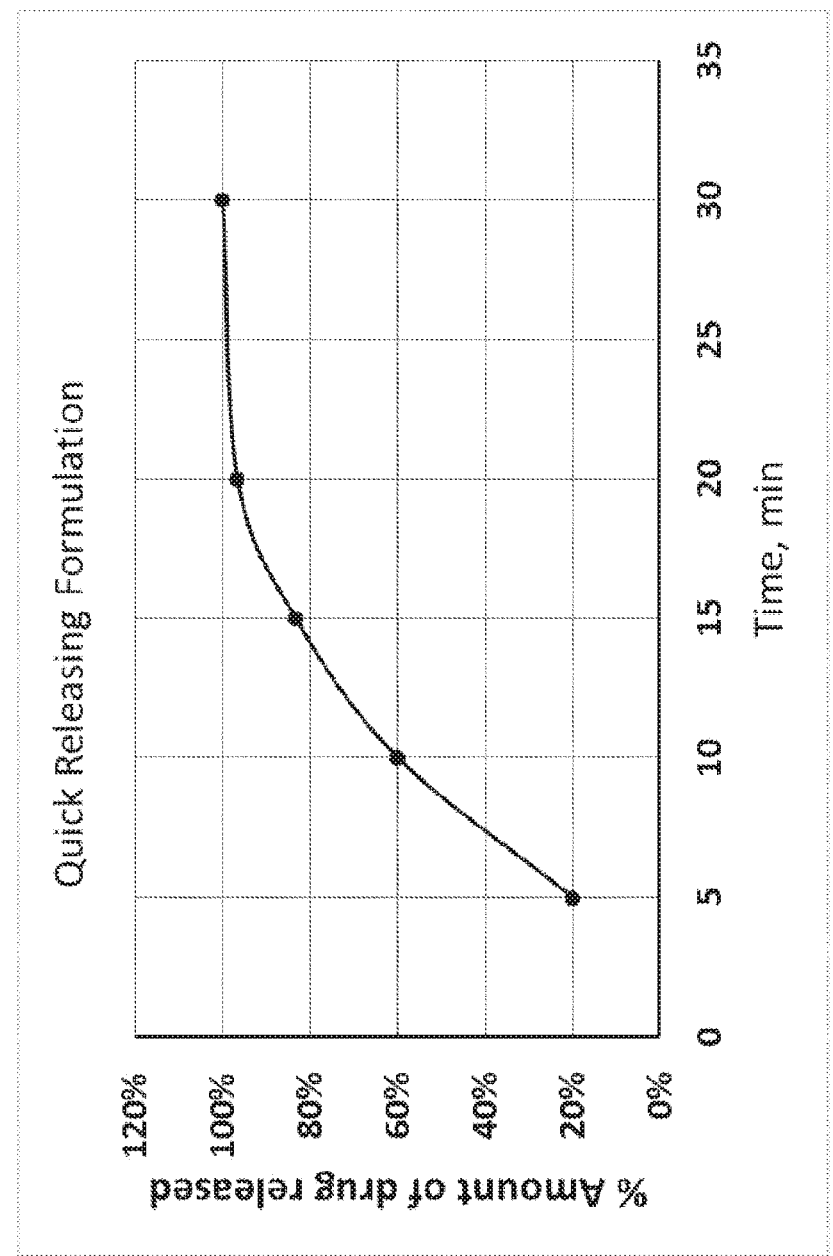
FIG. 1 shows that the drug was released in about 15-20 minutes of dissolution in in vivo drug release studies of formulation B (see Example 2).
Figure 2:
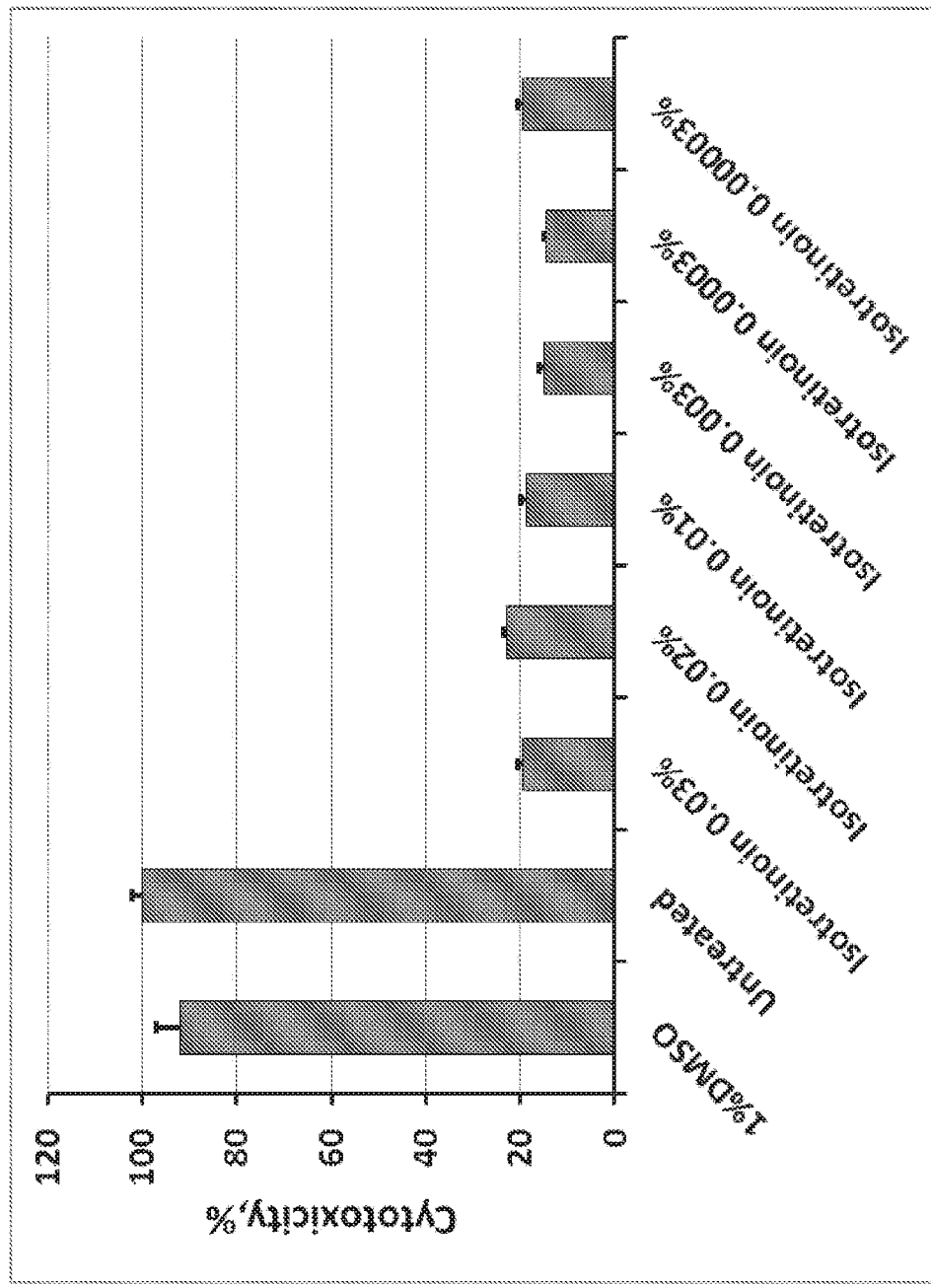
FIG. 2 shows the cytotoxicity in 2D cultured oral epithelial cells of different concentrations of isotretinoin.
Figure 3:
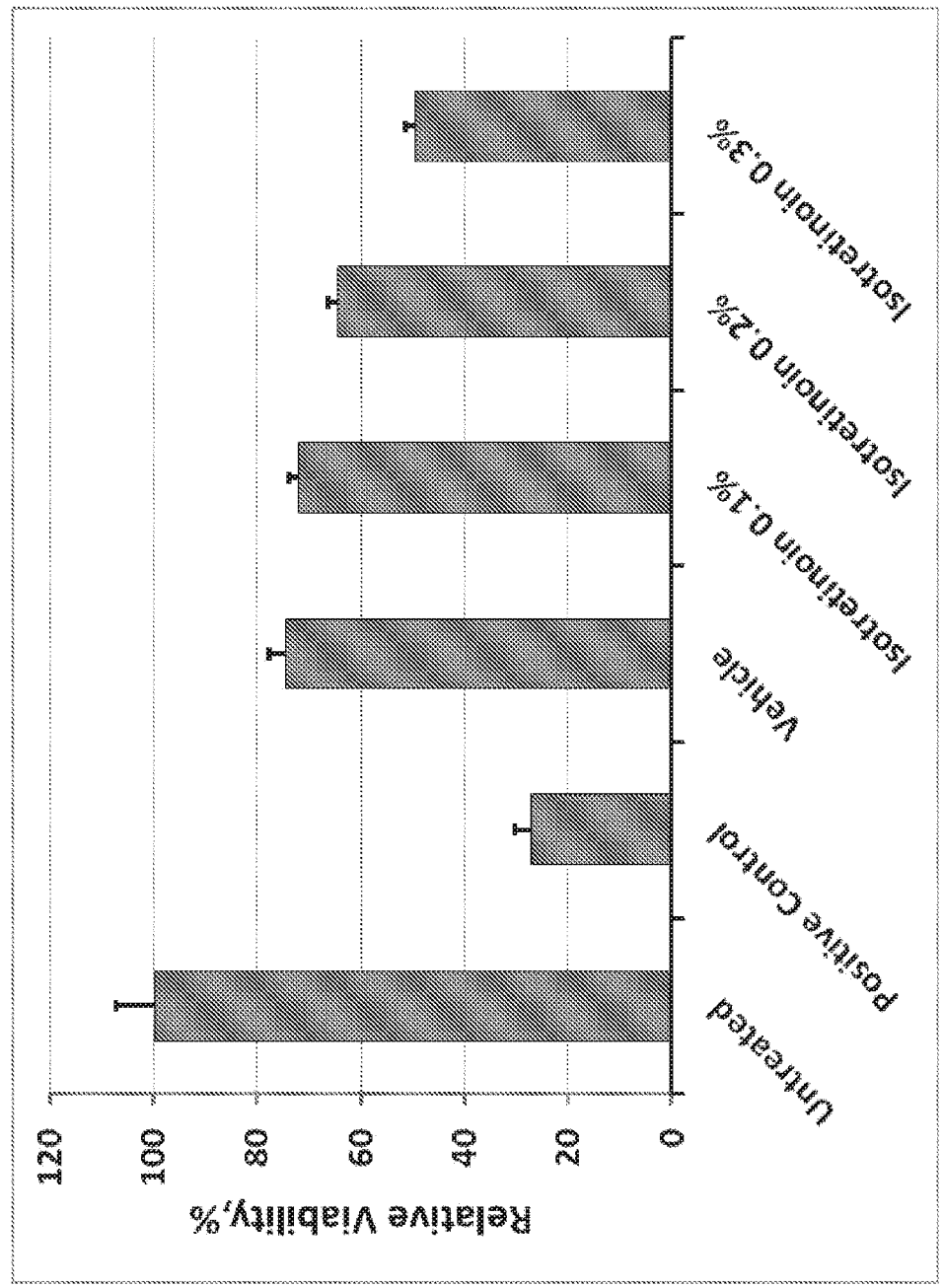
FIG. 3 shows the relative viability of 3D cultured gingival cells after 4 hours in the presence of 0.1%, 0.2% and 0.3% isotretinoin.

The present disclosure provides, in part, pharmaceutical formulations comprising isotretinoin or a pharmaceutically acceptable salt thereof, and a mucoadhesive polymer. The pharmaceutical formulations of the present disclosure are, in part, useful for the treatment of mucosal diseases, for example, oral leukoplakia. The dosage form of a disclosed pharmaceutical formulation may be a mucosal adhesive pharmaceutical film having isotretinoin, which may, for example, achieve substantially one directional drug release (e.g., absorption and/or mucosal permeation) to achieve effective local delivery to the intended tissue, such as an oral premalignant lesion and, for example, may avoid systemic uptake and/or deposition in adjacent tissues. Such provided formulations (e.g., films) may have minimal skin/mucosal irritation (or no irritation) when administered, and/or may provide minimal (or no) systemic availability of the drug.

Definitions

As used herein, the term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

"Individual," "patient," and "subject" are used interchangeably and include any animal, including mammals, e.g., mice, rats, other rodents, rabbits, dogs, cats, swine, cattle, sheep, horses, or primates, including humans.

"A patient in need," as used herein, refers to a patient suffering from any of the symptoms or manifestations of a mucosal disease, a patient who may suffer from any of the symptoms or manifestations of a mucosal disease, or any patient who might benefit from a method of the disclosure for treating a mucosal disease.

The terms "treat," "treatment," "treating" and the like are used herein to generally mean obtaining a desired pharmacological and/or physiological effect. The effect may be prophylactic in terms of completely or partially preventing a mucosal disease or symptom thereof and/or may be therapeutic in terms of partially or completely curing a mucosal disease and/or adverse effect attributed to a mucosal disease.

"Isotretinoin" as used herein refers to isotretinoin in the form of a free acid or its pharmaceutically acceptable salts. Isotretinoin may be referred to as 13-cis-retinoic acid or (2Z,4E,6E,8E)-3,7-dimethyl-9-(2,6,6-trimethylcyclohex-1-en-1-yl)nona-2,4,6,8-tetraenoic acid. Tretinoin (all-trans retinoic acid) and isotretinoin are geometric isomers and show reversible interconversion in vivo. The administration of one isomer can give rise to another. Other major metabolites of isotretinoin, such as 4-oxo-isotretinoin and its geometrical isomer 4-oxo-tretinoin, are also contemplated in the term "isotretinoin."

"Pharmaceutically acceptable" includes molecular entities and formulations that do not produce an adverse, allergic or other untoward reaction when administered to an animal, or a human, as appropriate. For human administration, preparations should meet sterility, pyrogenicity, and general safety and purity standards as required by FDA Office of Biologics standards.

The pharmaceutical formulations of the disclosure can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the disclosure is desirably a mammal in which treatment of a mucosal disease is desired.

The term "non-systemic" or "non-systemic administration" as used herein refers to an agent that has been administered locally and has only a local and/or topical effect to the affected area, e.g., oral mucosa. This includes the application of the pharmaceutical formulation described herein externally to the epidermis.

The term "local administration" as used herein refers to the administration of a pharmaceutical agent to or to the vicinity of a mucosa or a submucosa location in a subject by a non-systemic route.

The term "mucoadhesive polymer" as used herein refers to a polymer adhesive to mucus or mucous membrane. Mucoadhesive polymers are in general predominantly hydrophilic bioadhesive polymers. For example, a mucoadhesive polymer may be polyacrylic acids, xanthan gum, polyvinylpyrrolidone (PVP) (e.g., Kollidon 90 and Kollidon VA-64), carrageenan, pectin, sodium carboxymethylcellulose, alginate and pharmaceutically acceptable salts thereof, chitosan, polyvinyl alcohol, polyethylene oxide, or mixtures thereof. Such polyacrylic acids include, for example, crosslinked poly(acrylic acid) [e.g., carbopol] and polycarbophil. For example, polycarbophil may be Noveon, e.g., Noveon AA1.

The term "plasticizer" as used herein refers to a substance added to a material to produce or promote plasticity and flexibility and to reduce brittleness. The plasticizer can have surfactant properties such that it can act as a release modifier. For example, non-ionic detergents such as Brij 58 (polyoxyethylene (20) cetyl ether), and the like, can be used. Plasticizers impart flexibility to the dosage forms and can affect the release profile of the bioactive agent. For example, a plasticizer may be propylene glycol, polyethylene glycol (e.g., PEG 300, PEG 400, PEG 600, PEG 1000, PEG 1450, PEG 1500, PEG 3350, PEG 4500, PEG 8000), triacetin, triethyl citrate, castor oil, diethyl phthalate, or glycerin.

The term "antioxidant" as used herein refers to a molecule that inhibits the oxidation of other molecules. For example, an antioxidant may be, but not limited to, butylated hydroxytoluene, butylated hydroxyanisole, N-acetylcysteine, ascorbyl palmitate, 2,5-dihydroxybenzoic acid, propyl gallate, edetic acid, sodium edetate, L-cysteine, sodium metabisulfite, glutathione, cysteine, ascorbic acid and salts thereof, captopril, Na-ascorbate, $Na_2$-EDTA, Nae-EDTA-Ca, methimazole, quercetin, arbutin, aloesin, N-acetylglucoseamine, α-tocopheryl ferulate, MAP (Mg ascorbyl phosphate), sodium benzoate, L-phenylalanine, DMSA (succimer), DPA (D-penicillamine), trientine-HCl, dimercaprol, clioquinol, sodium thiosulfate, TETA (triethylenetetramine), TEPA (tetraethylenepentamine), curcumin, neocuproine, tannin, cuprizone, sodium hydrogen sulfite, lipoic acid, Trx-mimetic compounds (e.g., CB3, CB4, CB6), AD4, AD6, AD7, Vitamin E, di-tert-butyl methyl phenols, tert-butyl-methoxyphenols, polyphenols, tocopherols ubiquinones, or caffeic acid.

Pharmaceutical Formulations and Dosage Forms

The present disclosure relates, in part, to pharmaceutical formulations comprising isotretinoin or a pharmaceutically acceptable salt thereof, and a mucoadhesive polymer. In some embodiments, the pharmaceutical formulation is a mucosal adhesive pharmaceutical film. The pharmaceutical formulations of the present disclosure can be useful for the treatment of various mucosal diseases. In certain embodiments, the mucosal disease is an oral premalignant lesion. In some embodiments, the oral premalignant lesion is oral leukoplakia or oral erythroplakia.

In an embodiment, the mucosal adhesive pharmaceutical film comprises a mucoadhesive layer. In some embodiments, the mucoadhesive layer comprises a mucoadhesive polymer. In some embodiments, the mucosal adhesive pharmaceutical film optionally comprises an occlusive backing layer.

In an embodiment, the mucoadhesive polymer is hydrophilic, water-soluble, water-disintegrable and/or water-erodible. In an embodiment, the mucoadhesive polymer is a water-swellable polymer. In some embodiments, the mucoadhesive polymer is a mucoadhesive, hydrophilic biocompatible polymer.

In an embodiment, the mucoadhesive polymer is a polymer selected from the group consisting of Carbopol®, polycarbophil, xanthan gum, and polyvinylpyrrolidone (PVP). In an embodiment, the mucoadhesive polymer is selected from the group consisting of a chitosan, an alginate (e.g., sodium alginate, calcium alginate) and a high weight average molecular weight polyethylene oxide (PEO) (e.g., PolyOx N750, 1105, WSR-301).

In an embodiment, the mucoadhesive polymer is polycarbophil. e.g., Noveon AA1.

In an embodiment, the mucoadhesive polymer is a polyvinylpyrrolidone (PVP), e.g., povidone (e.g., Kollidon® 90).

In some embodiments, the PVP has a weight average molecular weight from about 1,000,000 g/mol to about 1,500,000 g/mol. In some embodiments, the PVP has a K value of 90.

In an embodiment, the mucoadhesive polymer is a polyvinyl alcohol (PVA) (e.g., Exceval, Selvol). In an embodiment, the mucoadhesive polymer is a polyethylene oxide (PEO). In some embodiments, the polyethylene oxide is a low molecular weight PEO (e.g., PolyOx N10). In an embodiment, the mucoadhesive polymer is a starch-based polymer (e.g., Lycoat).

In some embodiments, the mucoadhesive layer comprises a vinylpyrrolidone-vinyl acetate co-polymer and PVP. In some embodiments, the vinylpyrrolidone-vinyl acetate co-polymer has a weight average molecular weight of about 45,000 g/mol to about 70,000 g/mol.

In some embodiments, a first mucoadhesive polymer is present in the pharmaceutical formulation at a concentration of about 50% w/w, about 51% w/w, about 52% w/w, about 53% w/w, about 54% w/w, about 55% w/w, about 56% w/w, about 57% w/w, about 58% w/w, about 59% w/w, or about 60% w/w. In some embodiments, the mucoadhesive polymer is present in the pharmaceutical formulation at a concentration from about 50% w/w to about 60% w/w, about 51% w/w to about 60% w/w, about 52% w/w to about 60% w/w, about 53% w/w to about 60% w/w, about 54% w/w to about 60% w/w, about 55% w/w to about 60% w/w, about 56% w/w to about 60% w/w, about 57% w/w to about 60% w/w, about 58% w/w to about 60% w/w, about 59% w/w to about 60% w/w, about 50% w/w to about 59% w/w, about 50% w/w to about 58% w/w, about 50% w/w to about 57% w/w, about 50% w/w to about 56% w/w, about 50% w/w to about 55% w/w, about 50% w/w to about 54% w/w, about 50% w/w to about 53% w/w, about 50% w/w to about 52% w/w, about 50% w/w to about 51% w/w, about 51% w/w to about 52% w/w, 51% w/w to about 53% w/w, 51% w/w to about 54% w/w, 51% w/w to about 55% w/w, 51% w/w to about 56% w/w, 51% w/w to about 57% w/w, 51% w/w to about 58% w/w, 51% w/w to about 59% w/w, 52% w/w to about 53% w/w, 52% w/w to about 54% w/w, 52% w/w to about 55% w/w, 52% w/w to about 56% w/w, 52% w/w to about 57% w/w, 52% w/w to about 58% w/w, 52% w/w to about 59% w/w, 53% w/w to about 54% w/w, 53% w/w to about 55% w/w, 53% w/w to about 56% w/w, 53% w/w to about 57% w/w, 53% w/w to about 58% w/w, 53% w/w to about 59% w/w, 54% w/w to about 55% w/w, 54% w/w to about 56% w/w, 54% w/w to about 57% w/w, 54% w/w to about 58% w/w, 54% w/w to about 59% w/w, 55% w/w to about 56% w/w, 55% w/w to about 57% w/w, 55% w/w to about 58% w/w, 55% w/w to about 59% w/w, 56% w/w to about 57% w/w, 56% w/w to about 58% w/w, 56% w/w to about 59% w/w, 57% w/w to about 58% w/w, 57% w/w to about 59% w/w, or 58% w/w to about 59% w/w. In some embodiments, the first mucoadhesive polymer is PVP.

In an embodiment, the pharmaceutical formulation comprises a second mucoadhesive polymer. In some embodiments, the second mucoadhesive polymer is present in the pharmaceutical formulation at a concentration of about 10% w/w, about 11% w/w, about 12% w/w, about 13% w/w, about 14% w/w, about 15% w/w, about 16% w/w, about 17% w/w, about 18% w/w, about 19% w/w, or about 20% w/w. In some embodiments, the second mucoadhesive polymer is present in the pharmaceutical formulation at a concentration from 10% w/w to about 20% w/w, about 11% w/w to about 20% w/w, about 12% w/w to about 20% w/w, about 13% w/w to about 20% w/w, about 14% w/w to about 20% w/w, about 15% w/w to about 20% w/w, about 16% w/w to about 20% w/w, about 17% w/w to about 20% w/w, about 18% w/w to about 20% w/w, about 19% w/w to about 20% w/w, about 10% w/w to about 19% w/w, about 10% w/w to about 18% w/w, about 10% w/w to about 17% w/w, about 10% w/w to about 16% w/w, about 10% w/w to about 15% w/w, about 10% w/w to about 14% w/w, about 10% w/w to about 13% w/w, about 10% w/w to about 12% w/w, about 10% w/w to about 11% w/w, about 11% w/w to about 12% w/w, 11% w/w to about 13% w/w, 11% w/w to about 14% w/w, 11% w/w to about 15% w/w, 11% w/w to about 16% w/w, 11% w/w to about 17% w/w, 11% w/w to about 18% w/w, 11% w/w to about 19% w/w, 12% w/w to about 13% w/w, 12% w/w to about 14% w/w, 12% w/w to about 15% w/w, 12% w/w to about 16% w/w, 12% w/w to about 17% w/w, 12% w/w to about 18% w/w, 12% w/w to about 19% w/w, 13% w/w to about 14% w/w, 13% w/w to about 15% w/w, 13% w/w to about 16% w/w, 13% w/w to about 17% w/w, 13% w/w to about 18% w/w, 13% w/w to about 19% w/w, 14% w/w to about 15% w/w, 14% w/w to about 16% w/w, 14% w/w to about 17% w/w, 14% w/w to about 18% w/w, 14% w/w to about 19% w/w, 15% w/w to about 16% w/w, 15% w/w to about 17% w/w, 15% w/w to about 18% w/w, 15% w/w to about 19% w/w, 16% w/w to about 17% w/w, 16% w/w to about 18% w/w, 16% w/w to about 19% w/w, 17% w/w to about 18% w/w, 17% w/w to about 19% w/w, or 18% w/w to about 19% w/w. In some embodiments, the second mucoadhesive polymer is a vinylpyrrolidone-vinyl acetate co-polymer.

In an embodiment, isotretinoin or a pharmaceutically acceptable salt thereof is present in the pharmaceutical formulation in a concentration of at least about 0.05% w/w, at least about 0.1% w/w, at least about 0.15% w/w, at least about 0.2% w/w, at least about 0.25% w/w, at least about 0.3% w/w, at least about 0.35% w/w, at least about 0.4% w/w, at least about 0.45% w/w, or at least about 0.5% w/w. In some embodiments, isotretinoin or a pharmaceutically acceptable salt thereof is present in the pharmaceutical formulation in a concentration from about 0.05% w/w to about 0.5% w/w, about 0.1% w/w to about 0.5% w/w, about 0.15% w/w to about 0.5% w/w, about 0.2% w/w to about 0.5% w/w, about 0.25% w/w to about 0.5% w/w, about 0.3% w/w to about 0.5% w/w, about 0.35% w/w to about 0.5% w/w, least about 0.40% w/w to least about 0.5% w/w, about 0.45% w/w to about 0.5% w/w, about 0.05% w/w about 0.45% w/w, about 0.05% w/w to about 0.4% w/w, about 0.05% w/w to about 0.35% w/w, about 0.05% w/w to about 0.3% w/w, about 0.05% w/w to about 0.25% w/w, about 0.05% w/w to about 0.2% w/w, about 0.05% w/w to about 0.15% w/w, about 0.05% w/w to about 0.1% w/w, about 0.1% w/w to about 0.45%, about 0.1% w/w to about 0.4%, about 0.1% w/w to about 0.35%, about 0.1% w/w to about 0.3%, about 0.1% w/w to about 0.25%, about 0.1% w/w to about 0.2%, about 0.1% w/w to about 0.15%, about 0.15% w/w to about 0.45%, about 0.15% w/w to about 0.4%, about 0.15% w/w to about 0.35%, about 0.15% w/w to about 0.3%, about 0.15% w/w to about 0.25%, about 0.15% w/w to about 0.2%, about 0.2% w/w to about 0.45%, about 0.2% w/w to about 0.4%, about 0.2% w/w to about 0.35%, about 0.2% w/w to about 0.3%, about 0.2% w/w to about 0.25%, about 0.25% w/w to about 0.45%, about 0.25% w/w to about 0.4%, about 0.25% w/w to about 0.35%, about 0.25% w/w to about 0.3%, about 0.3% w/w to about 0.45%, about 0.3% w/w to about 0.4%, about 0.3% w/w to about 0.35%, about 0.35% w/w to about 0.45%, about 0.35% w/w to about 0.4%, or about 0.4% w/w to about 0.45%.

In an embodiment, isotretinoin or a pharmaceutically acceptable salt thereof is present in a concentration from about 0.1% w/w to about 0.3% w/w.

In an embodiment, isotretinoin or a pharmaceutically acceptable salt thereof is present in a concentration from about 0.2% w/w to about 0.4% w/w.

In an embodiment, isotretinoin or a pharmaceutically acceptable salt thereof is present in a concentration from about 0.05% to about 0.5% w/w or from about 0.1% to about 0.4% w/w.

In an embodiment, isotretinoin or a pharmaceutically acceptable salt thereof is present in a concentration of about 0.1% w/w.

In an embodiment, isotretinoin or a pharmaceutically acceptable salt thereof is present in a concentration of about 0.2% w/w.

In an embodiment, isotretinoin or a pharmaceutically acceptable salt thereof is present in a concentration of about 0.3% w/w.

In one aspect, provided herein is a mucosal adhesive pharmaceutical film comprising: a mucoadhesive layer comprising about 0.05% to about 0.5% w/w isotretinoin or a pharmaceutically acceptable salt thereof, and a mucoadhesive, hydrophilic biocompatible polymer; and optionally an occlusive backing layer.

In an embodiment, the pharmaceutical formulation further comprises a cellulose polymer.

In an embodiment, the cellulose polymer is a hydroxyalkyl cellulose polymer selected from the group consisting of hydroxypropylmethyl cellulose (HPMC), hydroxyethylpropyl cellulose (HEPC), hydroxybutylmethyl cellulose (HBMC), hydroxylpropyl cellulose (HPC), hydroxylethyl cellulose (HEC) and carboxymethyl cellulose (CMC).

In an embodiment, the cellulose polymer is HPMC, for example, HPMC E5 (e.g., 2-hydroxypropyl methyl ether cellulose).

In an embodiment, the pharmaceutical formulation/the mucoadhesive layer further comprises a plasticizer. In some embodiments, the pharmaceutical formulation/the mucoadhesive layer comprises 1, 2, 3, 4, or 5 plasticizers. In some embodiments, the total concentration of plasticizer in the pharmaceutical formulation/the mucoadhesive layer is about 5% w/w, about 7.5%, about 10% w/w, about 12.5% w/w, about 15% w/w, about 17.5% w/w, about 20% w/w, about 22.5% w/w, about 25% w/w, about 27.5% w/w, or about 30% w/w. In some embodiments, the total concentration of plasticizer in the pharmaceutical formulation/the mucoadhesive layer is from about 5% w/w to about 30% w/w, about 5% w/w to about 25% w/w, about 5% w/w to about 20% w/w, about 5% w/w to about 15% w/w, about 5% w/w to about 10% w/w, about 10% w/w to about 30% w/w, about 15% w/w to about 30% w/w, about 20% w/w to about 30% w/w, about 25% w/w to about 30% w/w, about 10% w/w to about 25% w/w, about 10% w/w to about 20% w/w, about 10% w/w to about 15% w/w, about 15% w/w to about 25% w/w, about 15% w/w to about 20% w/w, or about 20% w/w to about 25% w/w. In some embodiments, the pharmaceutical formulation/the mucoadhesive layer comprises propylene glycol and/or a PEG. In some embodiments, the PEG is PEG 400. In some embodiments, the PEG has a weight average molecular weight of about 380 g/mol to about 420 g/mol. In some embodiments, propylene glycol is present in the pharmaceutical formulation/the mucoadhesive layer at a concentration of about 4.5% w/w, about 4.6% w/w, about 4.7% w/w, about 4.8% w/w, about 4.9% w/w, about 5.0% w/w, about 5.1% w/w, about 5.2% w/w, about 5.3% w/w, about 5.4% w/w, or about 5.5% w/w. In some embodiments, propylene glycol is present in the pharmaceutical formulation/the mucoadhesive layer at a concentration from about 4.5% w/w to about 4.7% w/w, 4.5% w/w to about 4.9% w/w, 4.5% w/w to about 5.1% w/w, 4.5% w/w to about 5.3% w/w, 4.5% w/w to about 5.5% w/w, 4.7% w/w to about 4.9% w/w, about 4.7% w/w to about 5.1% w/w, about 4.7% w/w to about 5.3% w/w, about 4.7% w/w to about 5.5% w/w, about 4.9% w/w to about 5.1% w/w, about 4.9% w/w to about 5.3% w/w, about 4.9% w/w to about 5.5% w/w, 5.1% w/w to about 5.3% w/w, about 5.1% w/w to about 5.5% w/w, about 5.3% w/w to about 5.5% w/w, 4.6% w/w to about 4.8% w/w, 4.6% w/w to about 5.0% w/w, 4.6% w/w to about 5.2% w/w, 4.6% w/w to about 5.4% w/w, 4.8% w/w to about 5.0% w/w, about 4.8% w/w to about 5.2% w/w, about 4.8% w/w to about 5.4% w/w, about 5.0% w/w to about 5.2% w/w, about 5.0% w/w to about 5.4% w/w, 5.2% w/w to about 5.4% w/w, about 5.2% w/w to about 5.4% w/w, about 4.5% to about 5.5%, about 4.5% w/w to about 5.2, about 4.5% w/w to about 4.9% w/w, about 4.8% to about 5.5%, about 5.1% to about 5.5%, about 4.5% w/w to about 5.0% w/w, or about 5.0% w/w to about 5.5% w/w. In some embodiments, PEG 400 is present in the pharmaceutical formulation/the mucoadhesive layer at of concentration at about 15% w/w, about 15.5% w/w, about 16.0% w/w, about 16.5% w/w, about 17.0% w/w, about 17.5% w/w, about 18.0% w/w, about 18.5% w/w, about 19.0% w/w, about 19.5% w/w, or about 20.0% w/w. In some embodiments, is present in the pharmaceutical formulation/the mucoadhesive layer at a concentration from about 15.0% w/w to about 20% w/w, about 15.5% w/w to about 20% w/w, about 16.0% w/w to about 20% w/w, about 16.5% w/w to about 20% w/w, about 17.0% w/w to about 20% w/w, about 17.5% w/w to about 20% w/w, about 18.0% w/w to about 20% w/w, about 18.5% w/w to about 20% w/w, about 19.0% w/w to about 20% w/w, about 19.5% w/w to about 20% w/w, 15.0% w/w to about 20% w/w, about 15.5% w/w to about 20% w/w, about 16.0% w/w to about 20% w/w, about 16.5% w/w to about 20% w/w, about 17.0% w/w to about 20% w/w, about 17.5% w/w to about 20% w/w, about 18.0% w/w to about 20% w/w, about 18.5% w/w to about 20% w/w, about 15.0% w/w to about 19.5% w/w, about 15.0% w/w to about 19.0% w/w, about 15.0% w/w to about 18.5% w/w, about 15.0% w/w to about 18.0% w/w, about 15.0% w/w to about 17.5% w/w, about 15.0% w/w to about 17.0% w/w, about 15.0% w/w to about 16.5% w/w, about 15.0% w/w to about 16.0% w/w, about 15.0% w/w to about 15.5% w/w, about 16% w/w to about 18% w/w, or about 17% w/w to about 19% w/w.

In an embodiment, the mucoadhesive layer further comprises at least one of: an opacifying agent, a colorant, and/or an antioxidant.

In an embodiment, the mucoadhesive layer comprises an antioxidant. In some embodiments, the antioxidant is present in the pharmaceutical formulation at a concentration of about 0.2% w/w, about 0.3% w/w, about 0.4% w/w, about 0.5% w/w, about 0.6% w/w, about 0.7% w/w, or about 0.8% w/w. In some embodiments, the antioxidant is present in the pharmaceutical formulation at a concentration of about 0.40% w/w, about 0.41% w/w, about 0.42% w/w, about 0.43% w/w, about 0.44% w/w, about 0.45% w/w, about 0.46% w/w, about 0.47% w/w, about 0.48% w/w, about 0.49% w/w, or about 0.50% w/w. In some embodiments, the antioxidant is present in the pharmaceutical formulation at a concentration from about 0.2% w/w to about 0.8% w/w, 0.3% w/w to about 0.8% w/w, 0.4% w/w to about 0.8% w/w, 0.5% w/w to about 0.8% w/w, 0.6% w/w to about 0.8% w/w, 0.7% w/w to about 0.8% w/w, 0.2% w/w to about 0.7% w/w, 0.2% w/w to about 0.6% w/w, 0.2% w/w to about 0.5% w/w, 0.2% w/w to about 0.4% w/w, 0.2% w/w to about 0.3% w/w, about 0.3% w/w to about 0.7% w/w, about 0.3% w/w to about 0.6% w/w, about 0.3% w/w to about 0.5% w/w, or about 0.4% w/w to about 0.6% w/w. In some embodiments, the antioxidant is selected from the group comprising butylated hydroxytoluene (BHT), butylated hydroxyanisole, N-acetylcysteine, ascorbyl palmitate, 2,5-dihydroxybenzoic acid, propyl gallate, edetic acid, sodium edetate, L-cysteine, sodium metabisulfite, glutathione, cysteine, ascorbic acid and salts thereof, captopril, Na-ascorbate, $Na_2$-EDTA, $Na_2$-EDTA-Ca, methimazole, quercetin, arbutin, aloesin, N-acetylglucoseamine, α-tocopheryl ferulate, MAP (Mg ascorbyl phosphate), sodium benzoate, L-phenylalanine, DMSA (succimer), DPA (D-penicillamine), trientine-HCl, dimercaprol, clioquinol, sodium thiosulfate, TETA (triethylenetetramine), TEPA (tetraethylenepentamine), curcumin, neocuproine, tannin, cuprizone, sodium hydrogen sulfite, lipoic acid, CB3, CB4, CB6, AD4, AD6, AD7, Vitamin E, di-tert-butyl methyl phenols, tert-butyl-methoxyphenols, polyphenols, tocopherols ubiquinones, or caffeic acid. In some embodiments, the antioxidant is BHT.

In an embodiment, the mucoadhesive layer comprises an opacifying agent. In some embodiments, the opacifying agent is present in the pharmaceutical formulation at a concentration of about 4.0% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, or about 5.0% w/w. In some embodiments, the opacifying agent is present in the pharmaceutical formulation at a concentration from about 4.0% w/w to about 5% w/w, about 4.1% w/w to about 5% w/w, about 4.2% w/w to about 5% w/w, about 4.3% w/w to about 5% w/w, about 4.4% w/w to about 5% w/w, about 4.5% w/w to about 5% w/w, about 4.6% w/w to about 5% w/w, about 4.7% w/w to about 5% w/w, about 4.8% w/w to about 5% w/w, about 4.9% w/w to about 5% w/w, 4.0% w/w to about 4.1% w/w, 4.0% w/w to about 4.2% w/w, 4.0% w/w to about 4.3% w/w, 4.0% w/w to about 4.4% w/w, 4.0% w/w to about 4.5% w/w, 4.0% w/w to about 4.6% w/w, 4.0% w/w to about 4.7% w/w, 4.0% w/w to about 4.8% w/w, 4.0% w/w to about 4.9% w/w, about 4.2% w/w to about 4.8% w/w, about 4.4% w/w to about 4.6% w/w, or about 4.3% w/w to about 4.8% w/w. In some embodiments, the opacifying agent is titanium dioxide.

In an embodiment, the mucoadhesive layer comprises a colorant. In some embodiments, the colorant is present in the pharmaceutical formulation at a concentration of about 0.06% w/w, about 0.07% w/w, about 0.08% w/w, about 0.09% w/w, about 0.10% w/w, about 0.11% w/w, about 0.12% w/w, about 0.13% w/w, or about 0.14% w/w. In some embodiments, the colorant is present in the pharmaceutical formulation at a concentration from about 0.06% w/w to about 0.14% w/w, about 0.07% w/w to about 0.14% w/w, about 0.08% w/w to about 0.14% w/w, about 0.09% w/w to about 0.14% w/w, about 0.10% w/w to about 0.14% w/w, about 0.11% w/w to about 0.14% w/w, about 0.12% w/w to about 0.14% w/w, about 0.13% w/w to about 0.14% w/w, about 0.06% w/w to about 0.14% w/w, about 0.06% w/w to about 0.13% w/w, about 0.06% w/w to about 0.12% w/w, about 0.06% w/w to about 0.11% w/w, about 0.06% w/w to about 0.10% w/w, about 0.06% w/w to about 0.09% w/w, about 0.06% w/w to about 0.08% w/w, about 0.06% w/w to about 0.07% w/w, about 0.06% w/w to about 0.14% w/w, about 0.06% w/w to about 0.12% w/w, about 0.06% w/w to about 0.10% w/w, about 0.06% w/w to about 0.08% w/w, about 0.08% w/w to about 0.14% w/w, about 0.08% w/w to about 0.12% w/w, about 0.08% w/w to about 0.10% w/w, about 0.10% w/w to about 0.14% w/w, about 0.10% w/w to about 0.12% w/w, or about 0.12% w/w to about 0.14% w/w. In some embodiments, the colorant is FD&C Yellow No. 6.

Taste modifiers such as flavors, sweeteners, and taste masking agents can be incorporated into the dosage form/pharmaceutical formulation/the mucoadhesive layer to provide a pleasant taste and mouth-feel when the dosage form/pharmaceutical formulation is administered into the oral cavity. In some embodiments, the taste modifier is selected from the group comprising a flavoring agent, a sweetener, a taste making agent or a combination of any thereof. In some embodiments, the flavoring agent is selected from the group comprising natural mint, peppermint oil, a flavored oil, cocoa powder, or a combination thereof. In some embodiments, the sweetener is selected from the group comprising sodium saccharin, glucose, fructose, aspartame, sucralose, a steviosides, or a combination thereof. In some embodiments, the taste modifier is selected from the group comprising Cremophor® RH-40 (polyoxy 40 hydrogenated castor oil, BASF), clove oil, diglycerides, or a combination thereof. In some embodiments, the taste masking agent is selected from the group comprising Magnasweet 100 (mono-ammonium glycyrrhizinate, Mafco, Inc.), Eudragit E-100 (2-dimethylamino)ethyl methacrylate polymer, Evonikor any combination thereof. In some embodiments, the taste modifier is selected from the group comprising an essential oil of menthol, a water soluble extract of menthol, wintergreen, peppermint, sweet mint, spearmint, vanillin, cherry, chocolate, cinnamon, clove, lemon, orange, raspberry, rose, spice, violet, herbal, fruit, strawberry, grape, pineapple, peach, kiwi, papaya, mango, coconut, apple, coffee, plum, watermelon, nuts, durian, green tea, grapefruit, banana, butter or chamomile, sugar, dextrose, lactose, mannitol, sucrose, xylitol, maltitol, acesulfame potassium, talin, glycyrrhizin, sucralose, aspartame, saccharin, sodium saccharin, sodium cyclamate and honey. In some embodiments, the taste modifier is present in the pharmaceutical formulation at a concentration of about 2.0% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, or about 3.0% w/w. In some embodiments, the taste modifier is present in the pharmaceutical formulation at a concentration of about 2.30% w/w, about 2.31% w/w, about 2.32% w/w, about 2.33% w/w, about 2.34% w/w, about 2.35% w/w, about 2.36% w/w, about 2.37% w/w, about 2.38% w/w, about 2.39% w/w, or about 2.40% w/w. In some embodiments, the taste modifier is present in the pharmaceutical formulation at a concentration from about 2.0% w/w to about 3.0% w/w, about 2.1% w/w to about 3.0% w/w, about 2.2% w/w to about 3.0% w/w, about 2.3% w/w to about 3.0% w/w, about 2.4% w/w to about 3.0% w/w, about 2.5% w/w to about 3.0% w/w, about 2.6% w/w to about 3.0% w/w, about 2.7% w/w to about 3.0% w/w, about 2.8% w/w to about 3.0% w/w, about 2.9% w/w to about 3.0% w/w, about 2.0% w/w to about 2.9% w/w, about 2.0% w/w to about 2.8% w/w, about 2.0% w/w to about 2.7% w/w, about 2.0% w/w to about 2.6% w/w, about 2.0% w/w to about 2.5% w/w, about 2.0% w/w to about 2.4% w/w, about 2.0% w/w to about 2.3% w/w, about 2.0% w/w to about 2.2% w/w, about 2.0% w/w to about 2.1% w/w, about 2.1% w/w to about 2.3% w/w, about 2.1% w/w to about 2.5% w/w, about 2.1% w/w to about 2.7% w/w, about 2.1% w/w to about 2.9% w/w, about 2.1% w/w to about 2.4% w/w, about 2.1% w/w to about 2.6% w/w, about 2.2% w/w to about 2.4% w/w, about 2.2% w/w to about 2.6% w/w, about 2.2% w/w to about 2.8% w/w, about 2.2% w/w to about 2.5% w/w, about 2.2% w/w to about 2.7%, about 2.3% w/w to about 2.5% w/w, about 2.3% w/w to about 2.7% w/w, about 2.3% w/w to about 2.9% w/w, about 2.3% w/w to about 2.6%, about 2.3% w/w to about 2.8%, about 2.4% w/w to about 2.6% w/w, about 2.4% w/w to about 2.8% w/w, about 2.4% w/w to about 2.7% w/w, about 2.4% w/w to about 2.9% w/w, about 2.5% w/w to about 2.7% w/w, about 2.5% w/w to about 2.9% w/w, about 2.5% w/w to about 2.8% w/w, about 2.6% w/w to about 2.8% w/w, about 2.6% w/w to about 2.9% w/w, or about 2.7% w/w to about 2.9% w/w.

In an embodiment, the pharmaceutical formulation further comprises a soft backing. In some embodiments, the soft backing is a polymer film. In some embodiments, the soft backing is an occlusive backing layer. In some embodiments, the soft backing comprises an ethylene-vinyl acetate (EVA) polymer (e.g., CoTran 9715 EVA film). In some embodiments, the soft backing has a thickness of at least about 0.5 mils, about 1 mils, about 1.5 mils, about 2 mils, about 2.5 mils, about 3 mils, about 3.5 mils, about 4 mils, about 4.5 mils, or about 5 mils. In some embodiments, the soft backing has a thickness of between about 0.5 mils to about 5 mils, about 1 mils to about 5 mils, about 1.5 mils to about 5 mils, about 2 mils to about 5 mils, about 2.5 mils to about 5 mils, about 3 mils to about 5 mils, about 3.5 mils to about 5 mils, about 4 mils to about 5 mils, about 4.5 mils to about 5 mils, 0.5 mils to about 4.5 mils, about 1 mils to about 4.5 mils, about 1.5 mils to about 4.5 mils, about 2 mils to about 4.5 mils, about 2.5 mils to about 4.5 mils, about 3 mils to about 4.5 mils, about 3.5 mils to about 4.5 mils, about 4 mils to about 4.5 mils, about 0.5 mils to about 4 mils, about 1 mils to about 4 mils, about 1.5 mils to about 4 mils, about 2 mils to about 4 mils, about 2.5 mils to about 4 mils, about 3 mils to about 4 mils, about 3.5 mils to about 4 mils, about 0.5 mils to about 3.5 mils, about 1 mils to about 3.5 mils, about 1.5 mils to about 3.5 mils, about 2 mils to about 3.5 mils, about 2.5 mils to about 3.5 mils, about 3 mils to about 3.5 mils, about 0.5 mils to about 3 mils, about 1 mils to about 3 mils, about 1.5 mils to about 3 mils, about 2 mils to about 3 mils, about 2.5 mils to about 3 mils, about 0.5 mils to about 2.5 mils, about 1 mils to about 2.5 mils, about 1.5 mils to about 2.5 mils, about 2 mils to about 2.5 mils, about 0.5 mils to about 2 mils, about 1 mils to about 2 mils, about 1.5 mils to about 2 mils, about 0.5 mils to about 1.5 mils, about 1 mils to about 1.5 mils, or about 0.5 mils to about 1 mils.

In one aspect, the mucosal adhesive pharmaceutical film includes an occlusive backing layer. In some embodiments, the occlusive backing layer is substantially free of isotretinoin. In some embodiments, the occlusive backing layer is ingestible.

In an embodiment, the occlusive backing layer comprises one of more methacrylate based co-polymers. In some embodiments, the ingestible, occlusive backing layer comprises a polymer selected from the group consisting of poly(methacrylic acid-co-ethylacrylate) 1:1, poly(ethyl acrylate-co-methyl methacrylate-co-trimethylammonioethyl methacrylate chloride) 1:2:0.2 and combinations thereof.

In some embodiments, the mucoadhesive layer and/or the occlusive backing layer further comprise a plasticizer. In some embodiments, the occlusive backing layer comprises a plasticizer. In some embodiments, the plasticizer is propylene glycol and/or a PEG. In some embodiments, the PEG has a weight average molecular weight of about 380 g/mol to about 420 g/mol. In some embodiments, the PEG is PEG 400.

In some embodiments, the occlusive backing layer further comprises at least one of: an opacifying agent and/or a colorant. In some embodiments, the mucoadhesive layer comprises a colorant and the occlusive backing layer comprises a colorant different than that in the mucoadhesive layer. In some embodiments, the mucoadhesive layer is colored yellow. In some embodiments, the occlusive backing layer is colored red.

Also provided is a multilayered pharmaceutical formulation comprising a pharmaceutical formulation disclosed herein. In some embodiments, the multilayered pharmaceutical formulation comprises 2 layers, 3 layers, 4 layers or 5 layers. In some embodiments, the multilayered pharmaceutical formulation is a dual layer (2 layer) oral mucosal film.

In an embodiment, the multilayered pharmaceutical formulation comprises: (1) a first layer comprising isotretinoin or a pharmaceutically acceptable salt thereof and a mucoadhesive polymer; and (2) a second layer comprising an ingestible backing film. In some embodiments, the first layer is a mucoadhesive layer as described herein. In some embodiments, the second layer is a occlusive backing layer as described herein.

In an embodiment, the second layer of the multilayered pharmaceutical formulation comprises a methacrylate-based polymer. In some embodiments, the second layer of the multilayered formulation comprises 1, 2, 3, 4, or 5 methacrylate-based polymers. In some embodiments, the second layer of the multilayered formulation comprises 2 methacrylate-based polymers. In some embodiments, the total concentration of the 1, 2, 3, 4 or 5 polymethacrylate-based polymers present in the second layer of the multilayered pharmaceutical formulation is about 65% w/w, about 66% w/w, about 67% w/w, about 68% w/w, about 69% w/w, about 70% w/w, about 71% w/w, about 72% w/w, about 73% w/w, about 74% w/w, or about 75% w/w. In some embodiments, the total concentration of the 1, 2, 3, 4 or 5 methacrylate-based polymers present in the second layer of the multilayered pharmaceutical formulation is from about 65.0% w/w to about 75.0% w/w, about 66.0% w/w to about 75.0% w/w, about 67.0% w/w to about 75.0% w/w, about 68.0% w/w to about 75.0% w/w, about 69.0% w/w to about 75.0% w/w, about 70.0% w/w to about 75.0% w/w, about 71.0% w/w to about 75.0% w/w, about 72.0% w/w to about 75.0% w/w, about 73.0% w/w to about 75.0% w/w, about 74.0% w/w to about 75.0% w/w, about 65.0% w/w to about 74.0% w/w, about 65.0% w/w to about 73.0% w/w, about 65.0% w/w to about 72.0% w/w, about 65.0% w/w to about 71.0% w/w, about 65.0% w/w to about 70.0% w/w, about 65.0% w/w to about 69.0% w/w, about 65.0% w/w to about 68.0% w/w, about 65.0% w/w to about 67.0% w/w, about 65.0% w/w to about 66.0% w/w, about 66.0% w/w to about 68.0% w/w, about 66.0% w/w to about 70.0% w/w, about 66.0% w/w to about 72.0% w/w, about 66.0% w/w to about 74.0% w/w, about 66.0% w/w to about 69.0% w/w, about 66.0% w/w to about 71.0% w/w, about 67.0% w/w to about 69.0% w/w, about 67.0% w/w to about 71.0% w/w, about 67.0% w/w to about 73.0% w/w, about 67.0% w/w to about 70.0% w/w, about 67.0% w/w to about 72.0%, about 68.0% w/w to about 70.0% w/w, about 68.0% w/w to about 72.0% w/w, about 68.0% w/w to about 74.0% w/w, about 68.0% w/w to about 71.0%, about 68.0% w/w to about 73.0%, about 69.0% w/w to about 71.0% w/w, about 69.0% w/w to about 73.0% w/w, about 69.0% w/w to about 72.0% w/w, about 69.0% w/w to about 74.0% w/w, about 70.0% w/w to about 72.0% w/w, about 70.0% w/w to about 74.0% w/w, about 70.0% w/w to about 73.0% w/w, about 71.0% w/w to about 73.0% w/w, about 71.0% w/w to about 74.0% w/w, or about 72.0% w/w to about 74.0% w/w.

In an embodiment, the methacrylate-based polymer is an Eudragit® polymer, i.e. a poly(methacrylate). As contemplated herein such polymers form part of the disclosed films, for example, and not part of a common tablet coating. For example, in some embodiments, as disclosed herein, a disclosed poly(methacrylate) (such as a Eudragit® polymer) may be used as ingestible backing film for isotretinoin oral film to provide substantially one-direction permeation when the film is applied on oral mucosal tissues. In some embodiments, a contemplated poly(methacrylate) is Eudragit L100-55, Eudragit RL PO, or a combination of both, i.e., ethylacrylate-methacrylic acid polymer (e.g., (e.g., poly (methacrylic acid-co-ethylacrylate) 1:1) and/or co-polymers of ethyl acetate, methyl methacrylate and methacrylic acid. In some embodiments, the second layer of the multilayered pharmaceutical formulation comprises Eudragit L100-55 and Eudragit RL PO.

In some embodiments, an Eudragit L100-55 polymer (e.g., poly(methacrylic acid-co-ethylacrylate) 1:1) is present in the second layer of the multilayered pharmaceutical formulation at a concentration of about 40.0% w/w, about 40.5% w/w, about 41.0% w/w, about 41.5% w/w, about 42.0% w/w, about 42.5% w/w, about 43.0% w/w, about 43.5% w/w, about 44.0% w/w, about 44.5% w/w, or about 45.0% w/w. In some embodiments, the Eudragit L100-55 is present in the second layer of the multilayered pharmaceutical formulation at a concentration from about 40.0% w/w to about 45.0% w/w, about 40.5% w/w to about 45.0% w/w, about 41.0% w/w to about 45.0% w/w, about 41.5% w/w to about 45.0% w/w, about 42.0% w/w to about 45.0% w/w, about 42.5% w/w to about 45.0% w/w, about 43.0% w/w to about 45.0% w/w, about 45.0% w/w, about 43.5% w/w to about 45.0% w/w, about 44.0% w/w to about 45.0% w/w, about 44.5% w/w to about 45.0% w/w, about 40.0% w/w to about 44.5% w/w, about 40.0% w/w to about 44.0% w/w, about 40.0% w/w to about 43.5% w/w, about 40.0% w/w to about 43.0% w/w, about 40.0% w/w to about 42.5% w/w, about 40.0% w/w to about 42.0% w/w, about 40.0% w/w to about 41.5% w/w, about 40.0% w/w to about 41.0% w/w, about 40.0% w/w to about 40.5% w/w, about 40.5% w/w to about 41.5% w/w, about 40.5% w/w to about 42.5% w/w, about 40.5% w/w to about 43.5% w/w, about 40.5% w/w to about 44.5% w/w, about 40.5% w/w to about 42.0% w/w, about 40.5% w/w to about 43.0% w/w, about 41.0% w/w to about 42.0% w/w, about 41.0% w/w to about 43.0% w/w, about 41.0% w/w to about 44.0% w/w, about 41.0% w/w to about 42.5% w/w, about 41.0% w/w to about 43.5%, about 41.5% w/w to about 42.5% w/w, about 41.5% w/w to about 43.5% w/w, about 41.5% w/w to about 44.5% w/w, about 41.5% w/w to about 43.0%, about 41.5% w/w to about 44.0%, about 42.0% w/w to about 43.0% w/w, about 42.0% w/w to about 44.0% w/w, about 42.0% w/w to about 43.5% w/w, about 42.0% w/w to about 44.5% w/w, about 42.5% w/w to about 43.5% w/w, about 42.5% w/w to about 44.5% w/w, about 42.5% w/w to about 44.0% w/w, about 43.0% w/w to about 44.0% w/w, about 43.0% w/w to about 44.5% w/w, or about 43.5% w/w to about 44.5% w/w.

In some embodiments, an Eudragit RL PO (i.e., poly (ethyl acrylate, methyl methacrylate, trimethylammonio-ethyl methacrylate chloride 1:2:0.2) is present in the second layer of the multilayered pharmaceutical formulation at a concentration of about 25.0% w/w, about 25.5% w/w, about 26.0% w/w, about 26.5% w/w, about 27.0% w/w, about 27.5% w/w, about 28.0% w/w, about 28.5% w/w, about 29.0% w/w, about 29.5% w/w, or about 30.0% w/w. In some embodiments, the Eudragit RL PO is present in the second layer of the multilayered pharmaceutical formulation at a concentration from about 25.0% w/w to about 30.0% w/w, about 25.5% w/w to about 30.0% w/w, about 26.0% w/w to about 30.0% w/w, about 26.5% w/w to about 30.0% w/w, about 27.0% w/w to about 30.0% w/w, about 27.5% w/w to about 30.0% w/w, about 28.0% w/w to about 30.0% w/w, about 28.5% w/w to about 30.0% w/w, about 29.0% w/w to about 30.0% w/w, about 29.5% w/w to about 30.0% w/w, about 25.0% w/w to about 29.5% w/w, about 25.0% w/w to about 29.0% w/w, about 25.0% w/w to about 28.5% w/w, about 25.0% w/w to about 28.0% w/w, about 25.0% w/w to about 27.5% w/w, about 25.0% w/w to about 27.0% w/w, about 25.0% w/w to about 26.5% w/w, about 25.0% w/w to about 26.0% w/w, about 25.0% w/w to about 25.5% w/w, about 25.5% w/w to about 26.5% w/w, about 25.5% w/w to about 27.5% w/w, about 25.5% w/w to about 28.5% w/w, about 25.5% w/w to about 29.5% w/w, about 25.5% w/w to about 27.0% w/w, about 25.5% w/w to about 28.0% w/w, about 26.0% w/w to about 27.0% w/w, about 26.0% w/w to about 28.0% w/w, about 26.0% w/w to about 29.0% w/w, about 26.0% w/w to about 27.5% w/w, about 26.0% w/w to about 28.5%, about 26.5% w/w to about 27.5% w/w, about 26.5% w/w to about 28.5% w/w, about 26.5% w/w to about 29.5% w/w, about 26.5% w/w to about 28.0%, about 26.5% w/w to about 29.0%, about 27.0% w/w to about 28.0% w/w, about 27.0% w/w to about 29.0% w/w, about 27.0% w/w to about 28.5% w/w, about 27.0% w/w to about 29.5% w/w, about 27.5% w/w to about 28.5% w/w, about 27.5% w/w to about 29.5% w/w, about 27.5% w/w to about 29.0% w/w, about 28.0% w/w to about 29.0% w/w, about 28.0% w/w to about 29.5% w/w, or about 28.5% w/w to about 29.5% w/w.

In some embodiments, the second layer of the multilayered pharmaceutical formulation further comprises an opacifying agent. In some embodiments, the opacifying agent is titanium dioxide. In some embodiments, the opacifying agent is present in the second layer of the multilayered pharmaceutical formulation at a concentration of about 7.0% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, or about 8.0% w/w. In some embodiments, the opacifying agent is present in the second layer of the multilayered pharmaceutical formulation at a concentration from about 7.0% w/w to about 8% w/w, about 7.1% w/w to about 8% w/w, about 7.2% w/w to about 8% w/w, about 7.3% w/w to about 8% w/w, about 7.4% w/w to about 8% w/w, about 7.5% w/w to about 8% w/w, about 7.6% w/w to about 8% w/w, about 7.7% w/w to about 8% w/w, about 7.8% w/w to about 8% w/w, about 7.9% w/w to about 8% w/w, 7.0% w/w to about 7.1% w/w, 7.0% w/w to about 7.2% w/w, 7.0% w/w to about 7.3% w/w, 7.0% w/w to about 7.4% w/w, 7.0% w/w to about 7.5% w/w, 7.0% w/w to about 7.6% w/w, 7.0% w/w to about 7.7% w/w, 7.0% w/w to about 7.8% w/w, 7.0% w/w to about 7.9% w/w, about 7.2% w/w to about 7.8% w/w, about 7.4% w/w to about 7.6% w/w, or about 7.3% w/w to about 7.8% w/w.

In some embodiments, the second layer of the multilayered pharmaceutical formulation further comprises a colorant. In some embodiments, the colorant is a FD&C approved red colorant, e.g., 5404 FD&C Red No. 40. In some embodiments, the colorant is present in the second layer of the multilayered pharmaceutical formulation at a concentration of about 0.3% w/w, about 0.4% w/w, about 0.5% w/w, about 0.6% w/w, about 0.7% w/w, about 0.8% w/w, or about 0.9% w/w. In some embodiments, the colorant is present in the second layer of the multilayered pharmaceutical formulation at a concentration of about 0.45% w/w, about 0.46% w/w, about 0.47% w/w, about 0.48% w/w, about 0.49% w/w, about 0.50% w/w, about 0.51% w/w, about 0.52% w/w, about 0.53% w/w, about 0.54% w/w, or about 0.55% w/w. In some embodiments, the colorant is present in the second layer of the multilayered pharmaceutical formulation at a concentration from about 0.3% w/w to about 0.9% w/w, 0.4% w/w to about 0.9% w/w, 0.5% w/w to about 0.9% w/w, 0.6% w/w to about 0.9% w/w, 0.7% w/w to about 0.9% w/w, 0.8% w/w to about 0.9% w/w, 0.3% w/w to about 0.8% w/w, 0.3% w/w to about 0.7% w/w, 0.3% w/w to about 0.6% w/w, 0.3% w/w to about 0.5% w/w, 0.3% w/w to about 0.4% w/w, 0.4% w/w to about 0.8% w/w, 0.4% w/w to about 0.7% w/w, about 0.4% w/w to about 0.6% w/w, or 0.5% w/w to about 0.7% w/w.

In some embodiments, the second layer of the multilayered pharmaceutical formulation further comprises a plasticizer. In some embodiments, the second layer of the multilayered pharmaceutical formulation comprises 1, 2, 3, 4, or 5 plasticizers. In some embodiments, the total concentration of plasticizer in the second layer of the multilayered pharmaceutical formulation is about 5% w/w, about 7.5%, about 10% w/w, about 12.5% w/w, about 15% w/w, about 17.5% w/w, about 20% w/w, about 22.5% w/w, about 25% w/w, about 27.5% w/w, or about 30% w/w. In some embodiments, the total concentration of plasticizer in the second layer of the multilayered pharmaceutical formulation is from about 5% w/w to about 30% w/w, about 5% w/w to about 25% w/w, about 5% w/w to about 20% w/w, about 5% w/w to about 15% w/w, about 5% w/w to about 10% w/w, about 10% w/w to about 30% w/w, about 15% w/w to about 30% w/w, about 20% w/w to about 30% w/w, about 25% w/w to about 30% w/w, about 10% w/w to about 25% w/w, about 10% w/w to about 20% w/w, about 10% w/w to about 15% w/w, about 15% w/w to about 25% w/w, about 15% w/w to about 20% w/w, or about 20% w/w to about 25% w/w. In some embodiments, the second layer of the multilayered pharmaceutical formulation comprises propylene glycol and/or a PEG. In some embodiments, the second layer of the multilayered pharmaceutical formulation comprises propylene glycol and a PEG. In some embodiments, the PEG is PEG 400. In some embodiments, the PEG is present in the second layer of the multilayered pharmaceutical formulation at a concentration of about 12% w/w, about 13% w/w, about 14% w/w, about 15% w/w, about 16% w/w, or about 17% w/w. In some embodiments, the PEG is present in the second layer of the multilayered pharmaceutical formulation at a concentration of about 14.5% w/w, about 14.6% w/w, about 14.7% w/w, about 14.8% w/w, about 14.9% w/w, about 15.0% w/w, about 15.1% w/w, about 15.2% w/w, about 15.3% w/w, about 15.4% w/w, or about 15.5% w/w. In some embodiments, the PEG is present in the second layer of the multilayered pharmaceutical formulation at a concentration from about 12% w/w to about 17% w/w, about 13% w/w to about 17% w/w, about 14% w/w to about 17% w/w, about 15% w/w to about 17% w/w, about 16% w/w to about 17% w/w, about 12% w/w to about 16% w/w, about 12% w/w to about 15% w/w, about 12% w/w to about 14% w/w, about 12% w/w to about 13% w/w, about 13% w/w to about 14% w/w, about 13% to about 15% w/w, about 13% w/w to about 16% w/w, about 13% w/w to about 17% w/w, about 14% w/w to about 15% w/w, about 14% w/w to about 16% w/w, about 14% w/w to about 17% w/w, about 15% w/w to about 16% w/w, about 15% w/w to about 17% w/w, or about 16% w/w to about 17% w/w. In some embodiments, the propylene glycol is present in the second layer of the multilayered pharmaceutical formulation at a concentration of about 2% w/w, about 3% w/w, about 4% w/w, about 5% w/w, about 6% w/w, or about 7% w/w. In some embodiments, the propylene glycol is present in the second layer of the multilayered pharmaceutical formulation at a concentration of about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, or about 6.0% w/w. In some embodiments, the propylene glycol is present in the second layer of the multilayered pharmaceutical formulation at a concentration from about 2% w/w to about 7% w/w, about 3% w/w to about 7% w/w, about 4% w/w to about 7% w/w, about 5% w/w to about 7% w/w, about 6% w/w to about 7% w/w, about 2% w/w to about 6% w/w, about 2% w/w to about 5% w/w, about 2% w/w to about 4% w/w, about 2% w/w to about 3% w/w, about 3% w/w to about 4% w/w, about 3% to about 5% w/w, about 3% w/w to about 6% w/w, about 3% w/w to about 7% w/w, about 4% w/w to about 5% w/w, about 4% w/w to about 6% w/w, about 4% w/w to about 7% w/w, about 5% w/w to about 6% w/w, about 5% w/w to about 7% w/w, or about 6% w/w to about 7% w/w. In some embodiments, the second layer of the multilayered pharmaceutical formulation comprises about 15% w/w to about 16% w/w PEG 400 and about 5% w/w to about 6% w/w propylene glycol.

In an embodiment, more than 75%, 80%, 85%, 90%, 95% or 100% of the isotretinoin is released within 60 minutes using an USP 3 or a USP 7 dissolution apparatus. In some embodiments, more than 85% of the isotretinoin is released within 60 minutes using a USP 3 or 7 dissolution apparatus. In an embodiment, more than 75%, 80%, 85%, 90%, 95% or 100% of the isotretinoin is released within 20 minutes using a USP 3 and 7 dissolution apparatus. In some embodiments, more than 85% of the isotretinoin is released within 20 minutes using a USP 3 or 7 dissolution apparatus. In an embodiment, more than 75%, 80%, 85%, 90%, 95% or 100% of the isotretinoin is released within 15 minutes using a USP 3 and 7 dissolution apparatus. In some embodiments, more than 85% of the isotretinoin is released within 15 minutes using a USP 3 or 7 dissolution apparatus. In an embodiment, the drug release method is described in Example 1.

In some embodiments, a pharmaceutical formulation disclosed herein is stable at 25° C./60% RH for 1 month, 2 months, 3 months, 4 months, 5 months, 6 months, 7 months, 8 months, 9 months, 10 months, 11 months, or 12 months using ICH stability testing requirements. In some embodiments, a pharmaceutical formulation disclosed herein is stable at 40° C./75% RH for 1 month, 2 months, 3 months, 4 months, 5 months, 6 months, 7 months, 8 months, 9 months, 10 months, 11 months, or 12 months using ICH stability testing requirements. In some embodiments, the ICH stability testing requirements are Guideline ICH Q1A (R2) and ICH Q1E Evaluation of Stability Data.

Also provided herein is mucosal adhesive pharmaceutical film comprising: a mucoadhesive layer comprising about 0.1% w/w, about 0.2% w/w or about 0.3% w/w isotretinoin or a pharmaceutically acceptable salt thereof, about 12% w/w to about 15% w/w vinylpyrrolidone-vinyl acetate copolymer, about 53% w/w to about 57% w/w PVP, about 16% w/w to about 19% w/w PEG 400 and about 4% w/w to about 6% w/w propylene glycol; and an occlusive backing layer. In some embodiments, the occlusive backing layer comprising about 40% w/w to about 45% w/w poly(methacrylic acid-co-ethylacrylate) 1:1, about 25% w/w to about 30% w/w poly(ethyl acrylate-co-methyl methacrylate-co-trimethylammonioethyl methacrylate chloride) 1:2:0.2, about 13% w/w to about 16% w/w PEG 400 and about 4% w/w to about 6% w/w propylene glycol.

Also provided herein is a pharmaceutical formulation comprising: about 0.15% to about 0.35% w/w isotretinoin; and about 10% to about 20% w/w polycarbophil (e.g., Noveon).

Also provided herein is a pharmaceutical formulation comprising: about 0.2% w/w isotretinoin; and about 10% to about 20% w/w polycarbophil.

Also provided herein is a pharmaceutical formulation comprising: about 0.3% w/w isotretinoin; and about 20% to about 80% w/w of a dissolvable or an ingestible backing film.

Also provided herein is a multilayered pharmaceutical formulation, wherein the formulation comprises a first layer comprising: about 0.2% to about 0.4% w/w isotretinoin; and about 70% to about 80% w/w polyvinylpyrrolidone (PVP) (e.g. Kollidon); and a second layer comprising a backing film.

In one embodiment, the backing film is ingestible.

In one embodiment, the backing film comprises a polymethacrylate-based polymer, e.g., ethyl-acrylate-methacrylic acid polymer and/or copolymers of ethyl acrylate, methyl methacrylate and methacrylic acid, e.g., Eudragit, e.g., Eudragit L100-55, and Eudragit RL PO.

The films can be stand-alone or self-supporting, meaning the films have enough integrity so that there is no need to support them with additional backings, such as non-dissolvable films, such as polyethylene films.

Also, preservatives or stabilizers can be added when needed. Preservatives can include anti-microbial agents and non-organic compounds, and are exemplified by sodium benzoate, parabens and derivatives, sorbic acid and salts, propionic acids and salts, sulfur dioxide and sulfites, acetic acid and acetates, nitrites and nitrates, and the like.

In some embodiments, a dosage form is a single layer oral mucosal film. In some embodiments, a dosage form is a dual layer oral mucosal film.

The dosage form (single or dual layer film) can for example be square, rectangular, circular, oval, or any number of shapes. In some embodiments, the dosage form is square. Square dosage forms can be for example have sides about 1-4 inches in length. In some embodiments, the dosage form is a square with sides of a length about 0.25 inches, about 0.50 inches, about 0.75 inches, about 1 inch, about 1.25 inches, about 1.50 inches, about 1.75 inches, about 2 inches, about 2.25 inches, about 2.50 inches, about 2.75 inches, or about 3 inches. In some embodiments, the dosage form is circular. Circular (disk) dosage forms can be for example 1-4 inches in diameter. In some embodiments, the dosage form is circular with a diameter of about 0.25 inches, about 0.50 inches, about 0.75 inches, about 1 inch, about 1.25 inches, about 1.50 inches, about 1.75 inches, about 2 inches, about 2.25 inches, about 2.50 inches, about 2.75 inches, or about 3 inches.

In some embodiments, the dosage form (single or dual layer) is about 30 mil (0.762 mm) or less in thickness. In some embodiments, the dosage form (single or dual layer) is about 29 mil or less, or about 28 mil or less, about 27 mil or less, about 26 mil or less, about 25 mil or less, about 24 mil or less, about 23 mil or less, about 22 mil or less, about 21 mil or less, about 20 mil (0.508 mm) or less, about 19 mil or less, about 18 mil or less, about 17 mil or less, about 16 mil or less, about 15 mil or less, about 14 mil or less, about 13 mil or less, about 12 mil or less, about 11 mil or less, about 10 mil (0.254 mm) or less, about 9 mil or less or about 8 mil or less in thickness. In some embodiments, the dosage form (single or dual layer film) is about 1 mil or more, about 2 mil or more, about 3 mil or more, about 4 mil or more, about 5 mil or more, about 6 mil or more, about 7 mil or more, about 8 mil or more, about 9 mil or more, about 10 mil or more, about 11 mil or more, about 12 mil or more, about 13 mil or more, about 14 mil or more, or about 15 mil or more, about 16 mil or more, about 17 mil or more, about 18 mil or more, about 19 mil or more, or about 20 mil or more in thickness.

In some embodiments, the dosage form area (e.g., length× width, single or dual layer film) is about 20 cm$^2$ or less, about 19 cm$^2$ or less, about 18 cm$^2$ or less, about 17 cm$^2$ or less, about 16 cm$^2$ or less, about 15 cm$^2$ or less, about 14 cm$^2$ or less, about 13 cm$^2$ or less, about 12 cm$^2$ or less, about 11 cm$^2$ or less, about 10 cm$^2$ or less, about 9 cm$^2$ or less, about 8 cm$^2$ or less, about 7 cm$^2$ or less, about 6 cm$^2$ or less, about 5 cm$^2$ or less, about 4 cm$^2$ or less, about 3 cm$^2$ or less, or about 2 cm$^2$ or less. In certain embodiments, the dosage form area (single or dual layer) is about 1 cm$^2$ or more, about 2 cm$^2$ or more, about 3 cm$^2$ or more, about 4 cm$^2$ or more, or about 5 cm$^2$ or more.

In some embodiments, the dosage form area (single or dual layer film) is about equal to the area of an oral premalignant lesion. In some embodiments, the dosage form area (single or dual layer film) is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, about 95%, about 100%, about 100%, about 110%, about 120%, about 130%, about 140%, about 150%, about 160%, about 170%, about 180%, about 190%, about 200%, about 225%, about 250%, about 275%, about 300%, about 325%, about 350%, about 375%, about 400%, about 425%, about 450%, or about 500% larger than the area of an oral premalignant lesion. In some embodiments, the dosage form area (single or dual layer film) is about 2×, about 3×, about 4×, about 5×, about 6×, about 7×, about 8×, about 9×, about 10×, about 11×, about 12×, about 13×, about 14×, about 15×, about 16×, about 17×, about 18×, about 19×, about 20×, about 25×, about 30×, about 35×, about 40×, about 45×, about 50×, about 55×, about 60×, about 65×, about 70×, about 75×, about 80×, about 85×, about 90×, about 95×, about 100×, about 100×, about 110×, about 120×, about 130×, about 140×, about 150×, about 160×, about 170×, about 180×, about 190×, about 200×, about 225×, about 250×, about 275×, about 300×, about 325×, about 350×, about 375×, about 400×, about 425×, about 450×, or about 500× larger than the area of an oral premalignant lesion. It can be appreciated that a disclosed film may be customized in size (or capable of customization by e.g., simple cutting) to treat a particular size of lesion.

In some embodiments, the weight of a single dosage form (single or dual layer) is about 200 mg or less, about 190 mg or less, about 180 mg or less, about 170 mg or less, about 160 mg or less, about 150 mg or less, about 140 mg or less, about 130 mg or less, about 120 mg or less, about 110 mg or less, about 100 mg or less, about 90 mg or less, about 80 mg or less, about 70 mg or less, about 60 mg or less, about 50 mg or less, about 40 mg or less, or about 30 mg or less. In some embodiments, the weight of a single dosage form weight (single or dual layer) is about 20 mg or more, about 30 mg or more, about 40 mg or more, about 50 mg or more, about 60 mg or more, about 70 mg or more. about 80 mg or more, about 90 mg or more, about 100 mg or more, about 110 mg or more, about 120 mg or more, about 130 mg or more, about 140 mg or more, about 150 mg or more, about 160 mg or more, about 170 mg or more, about 180 mg or more, about 190 mg or more or about 200 mg or more.

In some embodiments, the weight of isotretinoin, or a pharmaceutically acceptable salt thereof, in the single dosage form is about 0.05 mg, about 0.075 mg, about 0.1 mg, about 0.125 mg, about 0.15 mg, about 0.175 mg, about 0.2 mg, about 0.225 mg, about 0.25 mg, about 0.275 mg, about 0.3 mg, about 0.325 mg, about 0.35 mg, about 0.375 mg, about 0.4 mg, about 0.425 mg, about 0.45 mg, 0.475 mg, or about 0.5 mg. In some embodiments, the weight of isotretinoin, or a pharmaceutically acceptable salt thereof, in the single dosage form is from about 0.05 mg to about 0.5 mg, about 0.075 mg to about 0.5 mg, about 0.1 mg to about 0.5 mg, about 0.125 mg to about 0.5 mg, about 0.15 mg to about 0.5 mg, about 0.175 mg to about 0.5 mg, about 0.2 mg to about 0.5 mg, about 0.225 mg to about 0.5 mg, about 0.25 mg to about 0.5 mg, about 0.275 mg to about 0.5 mg, about 0.3 mg to about 0.5 mg, about 0.325 mg to about 0.5 mg, about 0.35 mg to about 0.5 mg, about 0.375 mg to about 0.5 mg, about 0.4 mg to about 0.5 mg, about 0.425 mg to about 0.5 mg, about 0.45 mg to about 0.5 mg, about 0.475 mg to about 0.5 mg, about 0.05 mg to about 0.475 mg, about 0.05 mg to about 0.45 mg, about 0.05 mg to about 0.425 mg, about 0.05 mg to about 0.4 mg, about 0.05 mg to about 0.375 mg, about 0.05 mg to about 0.35 mg, about 0.05 mg to about 0.325 mg, about 0.05 mg to about 0.3 mg, about 0.05 mg to about 0.275 mg, about 0.05 mg to about 0.25 mg, about 0.05 mg to about 0.225 mg, about 0.05 mg to about 0.2 mg, about 0.05 mg to about 0.175 mg, about 0.05 mg to about 0.15 mg, about 0.05 mg to about 0.125 mg, about 0.05 mg to about 0.1 mg, about 0.05 mg to about 0.075 mg, about 0.1 mg to about 0.2 mg, about 0.1 mg to about 0.3 mg, about 0.1 mg to about 0.4 mg, about 0.15 mg to about 0.25 mg, about 0.15 mg to about 0.35 mg, about 0.15 mg to about 0.45 mg, about 0.2 mg to about 0.3 mg, about 0.2 mg to about 0.4 mg, about 0.25 mg to about 0.35 mg, about 0.25 mg to about 0.45 mg, about 0.3 mg to about 0.4 mg, or about 0.35 mg to about 0.45 mg.

In some embodiments, the distribution of isotretinoin, or pharmaceutically acceptable salt thereof, in the dosage form is about 0.025 mg/inch$^2$, about 0.05 mg/inch$^2$, about 0.075 mg/inch$^2$, about 0.1 mg/inch$^2$, about 0.125 mg/inch$^2$, about 0.15 mg/inch$^2$, about 0.175 mg/inch$^2$, about 0.2 mg/inch$^2$, about 0.225 mg/inch$^2$, about 0.25 mg/inch$^2$, about 0.275 mg/inch$^2$, about 0.3 mg/inch$^2$, about 0.325 mg/inch$^2$, about 0.35 mg/inch$^2$, about 0.375 mg/inch$^2$, about 0.4 mg/inch$^2$, about 0.425 mg/inch$^2$, about 0.45 mg/inch$^2$, about 0.475 mg/inch$^2$, or about 0.5 mg/inch$^2$. In some embodiments, the distribution of isotretinoin, or pharmaceutically acceptable salt thereof, in the dosage form is from about 0.025 mg/inch$^2$ to about 0.5 mg/inch$^2$, about 0.05 mg/inch$^2$ to about 0.5 mg/inch$^2$, about 0.075 mg/inch$^2$ to about 0.5 mg/inch$^2$, about 0.1 mg/inch$^2$ to about 0.5 mg/inch$^2$, about 0.125 mg/inch$^2$ to about 0.5 mg/inch$^2$, about 0.15 mg/inch$^2$ to about 0.5 mg/inch$^2$, about 0.175 mg/inch$^2$ to about 0.5 mg/inch$^2$, about 0.2 mg/inch$^2$ to about 0.5 mg/inch$^2$, about 0.225 mg/inch$^2$ to about 0.5 mg/inch$^2$, about 0.25 mg/inch$^2$ to about 0.5 mg/inch$^2$, about 0.275 mg/inch$^2$ to about 0.5 mg/inch$^2$, about 0.3 mg/inch$^2$ to about 0.5 mg/inch$^2$, about 0.325 mg/inch$^2$ to about 0.5 mg/inch$^2$, about 0.35 mg/inch$^2$ to about 0.5 mg/inch$^2$, about 0.375 mg/inch$^2$ to about 0.5 mg/inch$^2$, about 0.4 mg/inch$^2$ to about 0.5 mg/inch$^2$, about 0.425 mg/inch$^2$ to about 0.5 mg/inch$^2$, about 0.45 mg/inch$^2$ to about 0.5 mg/inch$^2$, about 0.475 mg/inch$^2$ to about 0.5 mg/inch$^2$, about 0.025 mg/inch$^2$ to about 0.475 mg/inch$^2$, about 0.025 mg/inch$^2$ to about 0.45 mg/inch$^2$, about 0.025 mg/inch$^2$ to about 0.425 mg/inch$^2$, about 0.025 mg/inch$^2$ to about 0.4 mg/inch$^2$, about 0.025 mg/inch$^2$ to about 0.375 mg/inch$^2$, about 0.025 mg/inch$^2$ to about 0.35 mg/inch$^2$, about 0.025 mg/inch$^2$ to about 0.325 mg/inch$^2$, about 0.025 mg/inch$^2$ to about 0.3 mg/inch$^2$, about 0.025 mg/inch$^2$ to about 0.275 mg/inch$^2$, about 0.025 mg/inch$^2$ to about 0.25 mg/inch$^2$, about 0.025 mg/inch$^2$ to about 0.225 mg/inch$^2$, about 0.025 mg/inch$^2$ to about 0.2 mg/inch$^2$, about 0.025 mg/inch$^2$ to about 0.175 mg/inch$^2$, about 0.025 mg/inch$^2$ to about 0.15 mg/inch$^2$, about 0.025 mg/inch$^2$ to about 0.125 mg/inch$^2$, about 0.025 mg/inch$^2$ to about 0.1 mg/inch$^2$, about 0.025 mg/inch$^2$ to about 0.075 mg/inch$^2$, about 0.025 mg/inch$^2$ to about 0.05 mg/inch$^2$, about 0.05 mg/inch$^2$ to about 0.15 mg/inch$^2$, about 0.05 mg/inch$^2$ to about 0.25 mg/inch$^2$, about 0.05 mg/inch$^2$ to about 0.35 mg/inch$^2$, about 0.05 mg/inch$^2$ to about 0.45 mg/inch$^2$, about 0.1 mg/inch$^2$ to about 0.2 mg/inch$^2$, about 0.1 mg/inch$^2$ to about 0.3 mg/inch$^2$, about 0.1 mg/inch$^2$ to about 0.4 mg/inch$^2$, about 0.15 mg/inch$^2$ to about 0.25 mg/inch$^2$, about 0.15 mg/inch$^2$ to about 0.35 mg/inch$^2$, about 0.15 mg/inch$^2$ to about 0.45 mg/inch$^2$, about 0.2 mg/inch$^2$ to about 0.3 mg/inch$^2$, about 0.2 mg/inch$^2$ to about 0.4 mg/inch$^2$, about 0.25 mg/inch$^2$ to about 0.35 mg/inch$^2$, about 0.25 mg/inch$^2$ to about 0.45 mg/inch$^2$, about 0.3 mg/inch$^2$ to about 0.4 mg/inch$^2$, or about 0.35 mg/inch$^2$ to about 0.45 mg/inch$^2$.

More than one dosage form can be used at each administration, such as 1-4 dosage forms per administration. Dosages of isotretinoin may be for example from 0.01 mg per administration to 100 mg per administration or from 0.01 mg per administration to 500 mg per administration or from 0.01 mg per administration to 1 g per administration. Administrations can be repeated as appropriate, and the release profile provided by preceding administrations.

Pharmaceutical Salts
Pharmaceutically Acceptable Salts

Pharmaceutically acceptable salts of isotretinoin used in the pharmaceutical formulations described herein are also contemplated for the uses described herein. "Pharmaceutically acceptable salt" refers to any salt of isotretinoin which retains its biological properties and which is not toxic or otherwise undesirable for pharmaceutical use. Pharmaceutically acceptable salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Pharmaceutically acceptable salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like.

Routes of Administration

The pharmaceutical formulations described herein can be administered via oral-mucosal delivery. In an embodiment, the pharmaceutical formulations described herein are administered to a subject in need thereof in the form of an oral mucoadhesive film. In some embodiments, the pharmaceutical formulations described herein are administered to a subject by placing the oral mucoadhesive film on the tongue of the subject. In some embodiments, the pharmaceutical formulations described herein are administered to a subject by placing the oral mucoadhesive film beneath the tongue of the subject. In some embodiments, the pharmaceutical formulations described herein are administered to a subject by placing the oral mucoadhesive film on the inside of the oral cavity of the subject, such as the left cheek, right cheek, hard palate, soft palate or any combination thereof.

Methods of Treatment

In one aspect, the disclosure provides a method of treating a mucosal disease in a patient in need thereof, the method comprising administering to the subject a pharmaceutical formulation comprising an effect amount of isotretinoin or a pharmaceutically acceptable salt thereof, and a mucoadhesive polymer, to thereby treat the disease.

In an embodiment, the mucosal disease is an oral premalignant lesion. In some embodiments, the oral premalignant lesion is oral leukoplakia or oral erythroplakia.

In one aspect, provided herein is a method of treating an oral premalignant lesion in a patient in need thereof comprising mucosally applying any of the films or compositions of any one of the provided herein to the patient, thereby administering an effective amount of the isotretinoin to the patient. In some embodiments, the oral premalignant lesion is oral leukoplakia or oral erythroplakia.

In some embodiments, mucosally applying comprises applying the mucoadhesive layer to the lesion on a mucosa of the mouth of the patient. In some embodiments, one or more lesions are treated comprising applying one or more films or compositions.

Contemplated methods may include administering a disclosed formulation once per week, twice per week, three times per week, four times per week, five times per week, six times per week, once a day, twice a day, three times a day, four times a day, or five times a day. In some embodiments, a formulation may be administered once per day. In some embodiments, a formulation may be administered for about 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 60 minutes. In some embodiments, a treatment regimen comprises mucosally applying any of the films or compositions of any one of the provided herein to the patient once per day for a period of 1 day, 5 days, 10 days, 15 days, 20 days, 25 days, 30 days, 1 month, 2 months 3 months, 4 months, 5 months, 6 months, 7 months, 8 months, 9 months, 10 months, 11 months, 12 months, 1 year, 2 years, 3 years, 4 years, or 5 years. In some embodiments, a treatment regimen comprises mucosally applying any of the films or compositions of any one of the provided herein to the patient once per day for the duration of the patient's life span. In some embodiments, a treatment regimen comprises mucosally applying any of the films or compositions of any one of the provided herein to the patient once per day until the oral premalignant lesion is resolved.

In one aspect, provided herein is a method of treating an oral premalignant lesion in a patient in need thereof comprising mucosally applying an orally adhesive film comprising about 0.1 to about 0.3 w/w or more of isotretinoin to the oral premalignant lesion for about 30 minutes once daily. It is understood that if a patient has more than one oral premalignant lesion, more than one film may be applied e.g., to each lesion.

In an embodiment, the size and shape of any one of the pharmaceutical formulations disclosed herein to be administered to a patient in need thereof is dependent on the size and shape of the oral premalignant lesion. In some embodiments, the size and shape of any one of the pharmaceutical formulations disclosed herein to be administered to a patient in need thereof is determined by a medically qualified professional (e.g., a doctor) treating the patient. In some embodiments, the size and shape of any one of the pharmaceutical formulations described herein is modified prior to administering the pharmaceutical formulation to a patient in need thereof. In some embodiments, the size and shape of any one of the pharmaceutical formulations described herein is modified by the medically qualified professional (e.g., a doctor) treating the patient.

Kits

In one aspect, the disclosure provides a kit for the treatment of a mucosal disease, comprising isotretinoin or a pharmaceutically acceptable salt thereof, and a mucoadhesive polymer. In an embodiment, a kit for the treatment of a mucosal disease comprising the formulation disclosed herein, is provided.

In one aspect, provided herein is a kit for suitable storage of an isotretinoin oral film. In some embodiments, the kit comprises a multilayered laminated pouch suitable for packaging any of the mucosal adhesive pharmaceutical films or pharmaceutical formulations provided herein and any of the mucosal adhesive pharmaceutical films or pharmaceutical formulations provided herein. In some embodiments, the multilayered laminated pouch comprises polyester and polyethylene film laminate. In some embodiments, the multilayered laminated pouch further comprises aluminum.

Provided herein, in an embodiment, is a product including a disclosed formulation contained in a kit. Contemplated kits may include a container. In some embodiments, the kit comprises a primary container and a secondary container. In some embodiments, the primary container is the multilayered laminated pouch provided herein. In some embodiments, the multilayered laminated pouch is sealed. In some embodiments, the multilayered laminated pouch comprises a single dose of a pharmaceutical formulation disclosed herein. In some embodiments, the single dose of a pharmaceutical formulation is a mucosal adhesive pharmaceutical film. In some embodiments, the secondary container is a box. In some embodiments, a box contains about 10, about 20, about 30, about 40, about 50, about 60, about 70, about 80, about 90, or about 100 pouched mucosal adhesive pharmaceutical films. In some aspects, contemplated kits may comprise instructions for use in treating a mucosal disease, e.g., a mucosal disease described herein and/or provide instructions for storage, e.g., instructions to store between 15° C. to 30° C.

EXAMPLES

Example 1. Drug Dissolution Testing Protocols

The purpose of this study was to develop a drug dissolution (drug release) method for isotretinoin oral mucoadhesive films. The criterion to achieve was that, at the end of dissolution, the dissolution rate was more than 85%.

The dissolution equipment used was Logan DISSO III-7 (USP 3 and 7 Dissolution Apparatus in one unit), manufactured by Logan Instruments, Somerset, N.J. Program was set to run the test as USP 3 Apparatus. Sampling was done with Logan DSC-37 System Controller/Logan SYP-8L Syringe Pump and Logan SCR-160 Sampler Collector.

Drug assay of dissolution media was determined by Agilent HPLC/UV system equipped with ChemStation using an in-house method. Medium for the dissolution study was N,N-Dimethyldodecylamine-N-oxide (DDAO) aqueous solution, 1% (w/w), prepared from 30% DDAO solution, as supplied by Sigma-Aldrich. Other operational parameters were: one film (1 inch×1 inch) in a cell, medium volume=200 mL, medium temperature=37° C., reciprocal speed=20 rpm, and stroke length=10 cm. Sampling times were 3, 6, 10, 20, 40 and 60 minutes.

Three film formulations were evaluated: 0.1% w/w, 0.2% w/w, and 0.3% w/w isotretinoin. Six cells (n=6) were used for each formulation.

Example 2. Mucoadhesive Formulation A

Formulation A for orally dissolvable and erodible thin flexible films with and without a soft (EVA polymer) backing film were formulated. This formulation was designed for slow release of the drug.

TABLE 1

0.2% Oral mucosal patch formulation

| Ingredient | Manufacturer | Function | wet g | dry g | dry % |
|---|---|---|---|---|---|
| Purified Water | | solvent | 42 | | |
| HPMC E5 (CAS RN 25322-68-3) | JRS Pharma | film matrix | 10.7 | 10.7 | 37.7% |
| Propylene Glycol | Dow Chemical | plasticizer | 8.2 | 8.2 | 28.9% |
| PEG 400 | Dow Chemical | plasticizer | 4.9 | 4.9 | 17.3% |
| Acetone | | solvent | 24 | | |
| Ethanol | | solvent | 26 | | |
| Noveon AA1 | Lubrizol | mucoadhesive | 4.5 | 4.5 | 15.9% |
| BHT | Spectrum | antioxidant | 0.03 | 0.0 | 0.1% |
| Isotretinoin | | active ingredient | 0.06 | 0.1 | 0.21% |
| Total | | | 120.39 | 28.4 | 100.00% |

All components were dissolved or dispersed in an acetone/ethanol/water (v/v/v ratio of 24/26/42) mixed solvent, and cast directly on EVA polymer backing film, or release liner, and dried at 75° C. for 15 min to produce dry films. For oral disc with the backing film, the casted/dried film is peeled off from the release liner to obtain a stand-alone film. These films are die-cut into 1 inch×1 inch unit dose discs, and tested accordingly.

In vitro drug release studies were conducted using formulation A and using the drug dissolution protocol described in Example 1. The results of the studies indicated that there was complete release of the drug within approximately 60 minutes.

Drug absorption studies were conducted on cultured human oral mucosal (buccal) tissues supplied by SkinAxis. The drug retained on the tissues after 24 hours was about 2.5 µg/cm$^2$.

Three-month accelerated stability studies of formulation A showed that formulation A was stable for 3 months at 25° C./60% RH and for 1 month at 40° C./75% RH. The stability study was carried out in accordance with ICH stability testing requirements using Guideline ICH Q1A (R2) and ICH Q1E Evaluation of Stability Data.

Example 3. Mucoadhesive Formulation B

Mucoadhesive formulation B was formulated to shorten the drug release time in the oral cavity and replace the non-ingestible EVA film with a dissolvable or ingestible backing film. The bioadhesive polymer of formulation A (i.e. Noveon AA1 (Polycarbophil)) was replaced with more water-soluble, polyvinylpyrrolidone (PVP)-based polymers. Formulation B comprises two layers: the mucoadhesive layer and an ingestible layer formulated with a polymethacrylate (Eudragit)-based polymer (Evonik), which is commonly used as a tablet film coating for oral solid formulations. The two-layer configuration was prepared by two-casting processes.

TABLE 2

0.3% isotretinoin formulation for quick-release

| Ingredient | Wet grams | Dry Parts | Dry % |
|---|---|---|---|
| Water | 4 | | |
| Ethanol | 35 | | |
| Kollidon 90F | 8 | 8 | 68.1% |
| Kollidon VA64 | 2 | 2 | 17.0% |
| Isotretinoin | 0.04 | 0.04 | 0.3% |
| PEG 400 | 1.5 | 1.5 | 12.8% |
| Propylene Glycol | 0.2 | 0.2 | 1.7% |
| Total | 50.74 | 11.74 | 100.0% |

Formulation B was prepared using the following procedure. In a 150 mL beaker, water, ethanol, PEG 400, and propylene glycol were added. While the mixture was being stirred, Kollidon VA 64 was added and then Kollidon 90F was added. The mixture was stirred for 10 minutes. Isotretinoin was added while the mixture was being stirred. The mixture was stirred until complete dissolution of all the solid components had occurred.

The wet solution was then cast onto an ingestible backing film using a wet thickness of about 50 mils (i.e. 1 mil is 1/1000$^{th}$ inch) of casting solution (see Table 3).

The casted wet film was then dried at 75° C. for 15 min and die-cut into 1 inch×1 inch unit dose discs, and tested accordingly.

TABLE 3

Ingestible Backing Film

| Ingredient | actual, g | Dry g | Dry % |
|---|---|---|---|
| Ethanol | 43.00 | | |
| Water | 10.00 | | |
| Eudragit L100-55 | 11.44 | 11.440 | 45.40% |
| Eudragit RL PO | 7.36 | 7.360 | 29.21% |
| Titanium dioxide | 1.00 | 1.000 | 3.97% |
| 5404 FD&C Red No. 40 | Tiny | | |
| PEG400 | 4.21 | 4.000 | 15.87% |
| Propylene glycol | 1.80 | 1.400 | 5.56% |
| Total | 78.81 | 25.20 | 100% |

The ingestible backing film was prepared by the following procedure. Ethanol, water, propylene glycol and PEG were added into a 150-mL beaker. Titanium dioxide and 5404 FD&C Red No. 40 were then added to the mixture during stirring. Eudragit polymer was then slowly added to the mixture while the mixture was being stirred. The mixture was stirred for 40 minutes until complete dissolution of the solid components had occurred. The wet solution (thickness of 30 mils) was coated on a polymer based release liner, (Loparex) release side, and was air-dried overnight. Later on, the wet solution containing the drug would be over-coated on this dried ingestible backing film.

In vitro drug release studies were conducted using the drug dissolution protocol described in Example 1 and the results indicated that complete release of the drug occurred within about 15-20 minutes, as shown in FIG. 1.

Example 4. Mucoadhesive Formulation C

Mucoadhesive formulation C is a quick-dissolving oral film prepared with a highly water-soluble polymer, polyethylene oxide (PEO, low molecular weight) as a film matrix polymer. Low molecular weight PEO polymer is PolyOx N-10 (molecular weight about 100,000), manufactured by Dow Chemical. The composition of formulation by ingredient and the function of each ingredient is described in Table 4.

TABLE 4

0.3% isotretinoin formulation C for quick-release

| Ingredient Name | Function | wet g | dry g | dry % |
|---|---|---|---|---|
| Isotretinoin | Active Ingredient | 0.09 | 0.09 | 0.30% |
| PolyOx N10 | Film matrix polymer | 21.0 | 21 | 70.61% |
| Propylene Glycol | Film Plasticizer | 4.0 | 4 | 13.45% |
| PEG 600 | Film Plasticizer | 3.5 | 3.5 | 11.77% |
| Aspartame | Sweetener | 0.5 | 0.5 | 1.68% |
| Peppermint Oil | Flavoring Agent | 0.5 | 0.5 | 1.68% |
| BHT | Antioxidant | 0.15 | 0.15 | 0.50% |
| Ethanol | Solvent | 15 | | |
| Water | Solvent | 50 | | |
| total | | 94.74 | 29.74 | 100% |

Propylene glycol, PEG 600, Peppermint Oil, water, and ethanol were added to a 100 mL beaker and stirred for five minutes. The PolyOx N10 was then gradually added into the beaker and stirring continued until complete dissolution of the PolyOx N10 had occurred. The BHT, aspartame and isotretinoin were then added to the solution and stirred until complete dissolution occurred.

Using a casting (draw-down) applicator, a wet thin film (30 mil thick) was cast (coat) onto a polyester release liner (e.g., 3M's Scotchpak 9744). The wet film was then dried in a forced-air oven at 90° C. for 10 min. After removing the dried film from the oven, the supporting release liner was discarded, and the neat oral film was then die-cut into a final unit dosage form (one inch by one inch oral) mucoadhesive film. Each unit was found to weigh about 100 mg and contained 0.3% of isotretinoin. In certain instances, the unit-dose film was contained in a sealed multi-laminated foil pouch.

The unit dose was tested to determine the dissolution rate of isotretinoin using the drug dissolution protocol described in Example 1. Total dissolution in water was found to occur in about two minutes.

Example 5. Mucoadhesive Formulation D

Mucoadhesive formulation D is a quick-dissolving oral film prepared using a highly water-soluble, film forming polymer, hydroxyl methyl propyl cellulose (HPMC) as a film matrix polymer. The HPMC polymer used was Methocel E5, manufactured by Dow Chemical. The composition of formulation by ingredient and the function of each ingredient is described in Table 5.

TABLE 5

0.3% isotretinoin formulation D for quick-release

| | Function | wet g | dry g | dry % |
|---|---|---|---|---|
| Methocel E5 | Film matrix polymer | 21 | 21 | 70.4% |
| Isotretinoin | Active ingredient | 0.09 | 0.09 | 0.30% |
| Propylene Glycol | Film plasticizer | 3.5 | 3.5 | 11.7% |
| PEG-400 | Film plasticizer | 3.5 | 3.5 | 11.7% |
| Aspartame | Sweetener | 0.5 | 0.5 | 1.7% |
| Peppermint Oil | Flavor | 0.5 | 0.5 | 1.7% |
| BHT | Antioxidant | 0.15 | 0.15 | 0.5% |
| Kolliphor EL | Solubilizer | 0.6 | 0.6 | 2.0% |
| Ethanol | Solvent | 20 | | |
| Water | Solvent | 50 | | |
| total | | 99.84 | 29.84 | 100% |

Propylene glycol, PEG 400, Peppermint Oil, Kolliphor EL (also known as Cremphor EL), water, and ethanol were added to a 200 mL beaker and stirred for five minutes. The Methocol E5 was then gradually added into the beaker and stirring continued until complete dissolution of the Methocol E5 had occurred. The BHT, aspartame and isotretinoin were then added to the solution and stirred until complete dissolution occurred.

Using a casting applicator, a wet thin film (30 mil thick) was cast (coat) onto a polyester release liner. The wet film was then dried in a forced-air oven at 90° C. for 10 min, to remove the solvents. After removing the dried film from the oven, the supporting release liner was discarded and the film was then die-cut into a final unit dosage form (one inch by one inch oral) mucoadhesive film. Each unit was found to weigh about 100 mg and contained 0.3% of isotretinoin. In certain instances, the unit-dose film was contained in a sealed multi-laminated foil pouch.

The unit dose was tested to determine the dissolution rate of isotretinoin using the drug dissolution protocol described in Example 1. Total dissolution in water was found to occur in about five minutes.

Example 6. Mucoadhesive Formulation E

This example demonstrates that oral films of isotretinoin with higher mucoadhesion and slower drug release properties were prepared using a combination of two water-swellable polymers, Carbopol (polyacrylic acid, supplied by Lubrizol) and xantham gum. Carbopol provides strong adhesion with the oral mucosal tissues, through ionic interactions, when wetted with saliva. The composition of formulation by ingredient and the function of each ingredient is described in Table 6.

TABLE 6

0.3% isotretinoin formulation E for sustained-release

| Ingredient | Function | wet g | dry g | dry % |
|---|---|---|---|---|
| Propylene Glycol | Film Plasticizer | 8 | 8.0 | 34.4% |
| PEG 400 | Film Plasticizer | 5 | 5.0 | 21.5% |
| Acetone | Solvent | 24 | | |
| Ethanol | Solvent | 29 | | |
| Xantham Gum | Matrix Polymer/ Bio-adhesive | 5.4 | 5.4 | 23.2% |
| Carbopol 971 | Matrix Polymer/ Bio-adhesive | 4.8 | 4.8 | 20.6% |
| Isotretinoin | Active ingredient | 0.07 | 0.07 | 0.30% |
| BHT | Antioxidant | 0.12 | 0.12 | 0.52% |
| Total | | 76.27 | 23.3 | 100.00% |

Propylene glycol, PEG 400, acetone, and ethanol were added to a 200 mL beaker and stirred for five minutes. The xantham gum was then gradually added into the beaker and stirring continued until complete dissolution occurred. In the same manner, the Carbopol 971 was added to the solution. The BHT and isotretinoin were then added to the solution and stirred until complete dissolution occurred.

Using a casting applicator, a wet thin film (40 mil thick) was cast (coat) onto a polyester release liner. The wet film was then dried in a forced-air oven at 90° C. for 10 min, to remove the solvents. After removing the dried film from the oven, the supporting release liner was discarded and the film was then die-cut into a final unit dosage form (one inch by one inch oral) mucoadhesive film. Each unit was found to weigh about 100 mg and contained 0.3% of isotretinoin. The films exhibited high elasticity and good muco-adhesion. In certain instances, the unit-dose film was contained in a sealed multi-laminated foil pouch.

The unit dose was tested to determine the dissolution rate of isotretinoin using the drug dissolution protocol described in Example 1. Total dissolution in water was found to occur in about 2 hours indicating sustained release of the drug.

Example 7. Mucoadhesive Formulation F

This example demonstrates that oral films of isotretinoin with higher mucoadhesion and slower drug release properties were prepared using medium molecular weight (300,000) polyethylene oxide (PEO), PolyOx N-750 (manufactured by Dow Chemical). Films prepared from medium to high MW PolyOx polymers are known to provide strong adhesion with the oral mucosal tissues when wetted with saliva. The composition of formulation by ingredient and the function of each ingredient is described in Table 7.

TABLE 7

0.3% isotretinoin formulation E for sustained-release

| Ingredient | Function | Wet grams | Dry grams | Dry % |
|---|---|---|---|---|
| Water | Solvent | 4 | | |
| Ethanol | Solvent | 30 | | |
| PolyOx N-750 | Matrix polymer/bio-adhesive | 10 | 10 | 75.8% |
| PEG 400 | Film plasticizer | 2 | 2 | 15.2% |
| Propylene Glycol | Film plasticizer | 1.2 | 1.2 | 9.1% |
| Isotretinoin | Active ingredient | 0.04 | 0.04 | 0.30% |
| BHT | Antioxidant | 0.07 | 0.07 | 0.53% |
| Total | | 47.2 | 13.2 | 100% |

Propylene glycol, PEG 400, water, and ethanol were added to a 200 mL beaker and stirred for five minutes. The PolyOx N-750 was then gradually added into the beaker and stirring continued until complete dissolution occurred. The BHT and isotretinoin were then added to the solution and stirred until complete dissolution occurred.

Using a casting applicator, a wet thin film (40 mil thick) was cast (coat) onto a polyester release liner. The wet film was then dried in a forced-air oven at 90° C. for 10 min, to remove the solvents. After removing the dried film from the oven, the supporting release liner was discarded and the film was then die-cut into a final unit dosage form (one inch by one inch oral) mucoadhesive film. Each unit was found to weigh about 100 mg and contained 0.3% of isotretinoin. In certain instances, the unit-dose film was contained in a sealed multi-laminated foil pouch.

The unit dose was tested to determine the dissolution rate of isotretinoin using the drug dissolution protocol described in Example 1. Total dissolution in water was found to occur in about 1 hour.

Example 8. Mucoadhesive Formulations G, H, I and J

Isotretinoin oral film formulations with various types of antioxidants were prepared, using the method and composition (except antioxidant or no antioxidant) based on Example C. Table 8 below summarizes the type and quantity of antioxidant used.

TABLE 8

Isotretinoin formulations comprising various antioxidants

| Antioxidant | Formulation C | Formulation G | Formulation H | Formulation I | Formulation J |
|---|---|---|---|---|---|
| BHT | 0.50% | | | | no antioxidant |
| Vitamin E | | 0.50% | | | |
| ascorbyl palmitate | | | 0.50% | | |
| propyl gallate | | | | 0.50% | |

The isotretinoin oral film formulations (formulation C, and formulations G to J) were packaged in multi-laminate foil pouches and subjected to a chemical stability study at 60° C. They were stored in an oven at 60° C. for two weeks, removed and assayed for drug content and possible degradants using a HPLC method. The test results showed that after 10 days at 60° C., samples of formulation J showed significant degradation (e.g., degradants were detected by HPLC), while formulations C, G, H, and I did not show any degradation. The tests showed that isotretinoin oral films formulated with 0.5% of BHT, vitamin E, ascorbyl palmitate, or propyl gallate were effective in enhancing the chemical stability of the isotretinoin (e.g., prevent it from oxidation). The stability study was carried out in accordance with ICH stability testing requirements using Guideline ICH Q1A (R2) and ICH Q1E Evaluation of Stability Data.

Example 9. Mucoadhesive Formulations K, L, M and N

Formulation K is a dual-layer thin oral adhesive film containing isotretinoin intended for application to oral mucosal tissues. The oral adhesive film (1 inch by 1 inch in size) has two layers: the drug-containing mucosal adhesive layer and a customer-formulated ingestible layer formulated with a polymethacrylate (Eudragit®)-based polymer, which is commonly used as a tablet film coating for oral solid dosage forms. The ingestible film serves as an occlusive backing to achieve one-directional drug release/absorption/mucosal permeation.

The composition of formulations K, L, M and N (0% w/w, 0.1% w/w, 0.2% w/w and 0.3% w/w isotretinoin) comprising a drug layer and a backing layer is given below in Table 9 and Table 10, respectively.

TABLE 9

Composition of the drug layer for formulations K, L, M and N (unit)

| Ingredient | Function | % per formulation K | % per formulation L | % per formulation M | % per formulation N |
|---|---|---|---|---|---|
| Kollidon 90F | Film matrix polymer | 56.10 | 56.05 | 55.99 | 55.94 |
| Kollidon VA64 | Film matrix polymer | 14.03 | 14.0 | 14.00 | 13.98 |

TABLE 9-continued

Composition of the drug layer for formulations K, L, M and N (unit)

| Ingredient | Function | % per formulation K | % per formulation L | % per formulation M | % per formulation N |
|---|---|---|---|---|---|
| Isotretinoin | Active Ingredient | 0.0 | 0.10 | 0.20 | 0.30 |
| Titanium dioxide | Opacity agent | 4.49 | 4.48 | 4.48 | 4.47 |
| FD&C Yellow #6 | Colorant | 0.09 | 0.09 | 0.09 | 0.09 |
| Nat Mint | Flavor | 2.38 | 2.38 | 2.38 | 2.38 |
| BHT | Antioxidant | 0.46 | 0.46 | 0.46 | 0.46 |
| PEG 400 | Plasticizer | 17.53 | 17.52 | 17.50 | 17.48 |
| Propylene Glycol | Plasticizer | 4.91 | 4.90 | 4.90 | 4.89 |

TABLE 10

Composition of the non-drug (backing) layer for all formulations (unit)

| Ingredient | Function | % per film |
|---|---|---|
| Eudragit L100-55 | Polymer | 43.66% |
| Eudragit RL PO | Polymer | 27.71% |
| Titanium Dioxide | Opacity Agent | 7.59% |
| FD&C Red No. 40 | Colorant | 0.53% |
| PEG400 | Plasticizer | 15.19% |
| Propylene glycol | Plasticizer | 5.32% |

The stability of formulations L, M and N was carried out according to ICH stability testing requirements using Guideline ICH Q1A (R2) and ICH Q1E Evaluation of Stability Data.

Formulations L, M and N were stored in sealed foil laminate pouches, as disclosed herein, under storage conditions of 25° C./60% RH and 40° C./75% RH. Samples of the different formulations were removed from storage at 0, 1, 2, 3 and 6 months and assayed for drug content and possible degradants using a HPLC method. The acceptance criteria used in the stability study were: (1) a moisture content of not more than 7.5% (w/w), (2) drug content between 90-110% of original drug content, (3) individual degradant content not more than 0.5% (w/w) and (4) total degradant content no more than 3% (w/w).

Formulations L, M and N were all found to be stable at both 25° C./60% RH and 40° C./75% RH for up to 6 months.

Example 10. Protocol for Permeation Experiments Using Cultured Tissues

Receiver fluid was prepared according to the following procedure. The assay medium is pre-warmed to 37° C. Phosphate buffer solution (PBS) of pH 6.8 is used for oral cavity tissues. Phosphate buffer solution of pH 7.4 is used for cultured skin. The medium is pipetted into each well of the plates. The volume of the added medium should be just enough to cover the tissue membrane (0.3 to 0.5 mL, depending on whether they are 6-well, 12-well, or 24-well plates). The plates are labeled to accommodate sampling at desired time points. For example, the wells are labeled as 0.5, 1.0, 1.5, 2.0, and 2.5 hours. This method involves moving the tissues from well to well at the appropriate time point. An alternative method is to remove all receiver solution at the appropriate time point (receiver solution is saved for later analysis) and refill the well with fresh receiver solution.

0.5 mL of donor solution is used on the donor well or appropriate matching sized patch or film. The articles should be in good contact with the tissue surfaces.

The permeability experiment was conducted according to the following procedure. The donor solution was pipetted onto the tissue or the die-cut patch or film was placed onto the tissue. The plates were returned to the incubator. After the first elapsed permeation time, the tissues were moved to the next wells. The receiver media in HPLC vials were collected and kept in the refrigerator. The tissues were moved after the next few time-points of total elapsed time.

Example 11. Mucosal Tissue Permeation/Deposition Kinetic Study

An in vitro mucosal tissue permeation/deposition kinetic study was conducted with the 0.1%, 0.2%, and 0.3% isotretinoin oral adhesive film formulations of Example 9. Two 6-well plates were provided with each well containing a 1-inch tissue. One 1-inch diameter film was placed on the oral mucosal tissue. The permeated and deposited amounts of isotretinoin were determined at Day 1, 2 and 3 using ethanol extraction procedure, and the concentrations were assayed by HPLC. Results are provided in Table 11. Each value reported is the average of 3 cell measurements. The preparation of the cultured tissues used in the kinetic study is described in Example 10.

TABLE 11

Results from In Vitro Mucosal Tissue Permeation/Deposition Kinetic Study

| | Drug Deposition in Skin, µg/cm$^2$ | | | |
|---|---|---|---|---|
| Day | 0.1% isotretinoin formulation | 0.2% isotretinoin formulation | 0.2% isotretinoin formulation | 0.3% isotretinoin formulation |
| 1 | 2.63 | 3.83 | nd | 3.39 |
| 2 | 3.05 | 4.08 | nd | 4.09 |
| 3 | 3.32 | 4.30 | 3.98 | 3.75 |

This in vitro study of oral mucosal tissue suggests that isotretinoin can be more highly concentrated in the tissue if a 0.3% film is administered directly to the oral lesion, with an average mucosal tissue concentration of 3.75 µg/cm$^2$, but minimal penetration outside the tissue.

Example 12. In Vitro Cytotoxicity and Irritation Testing of CCP-042 on Oral Epithelial Cells For this study, three patches of CCP-042 oral adhesive film (0.1%, 0.2%, and 0.3%) were used. Untreated samples were tested in parallel as negative controls.
Evaluation of Cytotoxicity in 2D Cultured Oral Epithelial Cells Human gingival keratinocytes derived from a single donor were cultured at 37° C. with 5% CO2, and 95% humidity in a 96-well plate for cytotoxicity evaluation. Cells were incubated in the presence of seven concentrations of isotretinoin ranging from 0.3 to 0.00003% for 24 h in triplicate. Untreated cells were used as baseline control. Cytotoxicity was evaluated using the Cell Titer96 Aqueous One (Promega, Wis., USA) basic test according to manufacturer's instructions using an absorbance of 490 nm for the final colorimetric readings. The concentration of isotretinoin showing the inhibition of viability of more than 20% of the control values was considered cytotoxic. At all tested concentrations, isotretinoin was toxic to gingival cells (FIG. 1).

Skin Irritation Testing of Isotretinoin Formulations in 3D Cultured Oral Epithelial Cells Human oral mucosa 3D models (composed of human gingival keratinocytes) were exposed topically to CCP-042 oral adhesive film (0.1%, 0.2%, and 0.3%) for 4 hr before viability assessment. Cell viability was measured by MTT assay on tissues, in triplicate. 1% Triton X-100 was used as positive control. The reduction of the viability of tissues exposed to formulations as compared to that of PBS-treated negative controls were used to predict the skin irritation potential using European Union (EU) and Globally Harmonized System (GHS) classifications, which define an irritant as a substance that reduces the viability of the exposed tissue to less than 50% of the viability of untreated controls.

Significant changes were observed at all the tested isotretinoin concentrations relative to the untreated tissues. However, with respect to the vehicle control, only the highest tested formulation (0.3%) decreased tissue viability, thus suggesting that isotretinoin is not toxic at concentrations of 0.1% and 0.2%.

Example 13. Acute Oral Irritation in Hamster Cheek Model

A non-GLP irritation study was conducted in Golden Syrian hamsters to evaluate local tolerance and acute toxicity associated with two daily applications of three dose strengths of CCP-042 (0.1, 0.2, and 0.3%) compared to a placebo (vehicle control) followed by a 3-day recovery period.

Twenty-four (24) young adult hamsters (12 males and 12 females) were used in this study. CCP-042 oral adhesive films were administered by applying the drug-side of the film to the left buccal mucosa of the cheek pouch and allowing it to dissolve. The clean everted pouch was examined and scored according to the modified Draize "Scale for Scoring Oral Mucosa". The right cheek received no treatment. Drinking water was withheld from the animals 1 hour before the first dose and until 2 hours after the second dose. The second dose was administered 4 hours after the first dose. Safety and local tolerability were assessed by monitoring signs of toxicity before each dosing interval, twice per day on the day of dosing and once per day for the 3 days of recovery (total of 4 days). Any adverse effect of the test articles was assessed by behavioral response of the animals. Abnormal findings were recorded. All animals were observed at least twice daily for sign of viability. Scoring for buccal mucosal was performed 3 times daily throughout the dosing period. Scoring for buccal mucosal irritation continued at 24, 48 and 72 hours following the final dose to assess reversibility. After the pouch was rinsed and clear of food particles and while it was everted, observations were made and recorded by scalar notation from "0" to "4". Results are provided below. Buccal mucosa irritation average score was calculated using the group erythema scores and the group edema scores and determined the average for each group and sex at each time period.

Twenty-four animals (twelve males and twelve females) were randomly assigned to each of the following test groups (Table 12):

TABLE 12

Group Average Mucosal Irritation Scores in Hamster Cheek Tolerability Study

| Time Post-application (h) | Buccal Mucosal Irritation Average Score | | | |
|---|---|---|---|---|
| | Vehicle Control (0%) | Low Dose (0.1%) | Mid Dose (0.2%) | High Dose (0.3%) |
| 1 (1st dose) | 0 | 0.15 | 0.25 | 0.35 |
| 5 (2nd dose) | 0 | 0.15 | 0.45 | 0.5 |
| 24 | 0 | 0 | 0.25 | 0.35 |
| 48 | 0 | 0 | 0.25 | 0.1 |
| 72 | 0 | 0 | 0.35 | 0 |

The Group 2 (0.1% dose—low dose) Average Erythema Score ranged from 0 to 0.3; Average Edema Score was 0; and Average Mucosal Irritation Score ranged from 0 to 0.15 indicating that the test article was not considered an irritant at this dose.

The Group 3 (0.2% dose—mid dose) Average Erythema Score ranged from 0.2 to 0.7; Average Edema Score ranged from 0 to 0.5; and Average Mucosal Irritation Score ranged from 0.25 to 0.45. Scores observed at 48 and 72 hours were attributed to observations recorded for animal 3815 interpreted to be due to mechanical injury during dosing, therefore the test article was not considered an irritant at this dose.

The Group 4 (0.3% dose—high dose) Average Erythema Score ranged from 0 to 0.8; Average Edema Score ranged from 0 to 0.2; and Average Mucosal Irritation Score ranged from 0 to 0.50, with complete resolution of both edema and erythema at 72 hours after test article administration, therefore the test article was not considered an irritant at this dose level.

There were no mortalities during the study. Slight swelling of the face observed in one male in the Group 3 was attributed to the dosing procedure related mechanical injury and not considered a test article effect.

Following the last day's observation (Day 4), all animals were euthanized and the right and left cheek pouch from all animals were examined microscopically. Evaluation of the oral mucosa of the cheek pouch included, but not limited to, evidence of edema, inflammatory cell infiltrates or inflammation, epithelial and vascular changes. There was no evidence of test substance-related irritation of the oral mucosa of the cheek pouch.

Under the conditions of this study, the application of CCP-042 films at the doses up to 0.3% in male and female Golden Syrian hamsters did not produce buccal mucosal irritation.

Example 14. Drug Release Study for Mucoadhesive Formulations L, M and N

Drug dissolution profiles of isotretinoin oral mucoadhesive films comprising formulations L, M, and N (Example 9) were carried out using the drug dissolution protocols described in Example 1.

The drug release data (%), averaged values (AVE), along with standard deviation (STD) and % RSD, for the three formulations tested at the pre-selected sampling times are given in Table 13.

TABLE 13

Drug release data for Formulations L, M and N

| | Formulation L | | | Formulation M | | | Formulation N | | |
|---|---|---|---|---|---|---|---|---|---|
| Time (min) | AVE drug released | STD | % RSD | AVE drug released | STD | % RSD | AVE drug released | STD | % RSD |
| 0 | 0.0 | n/a | n/a | 0.0 | n/a | n/a | 0.0 | n/a | n/a |
| 3 | 27.5% | 7.3% | 26.7% | 21.3% | 5.8% | 27.1% | 25.2% | 12.7% | 50.6% |
| 6 | 84.4% | 3.3% | 3.9% | 78.9% | 4.4% | 5.6% | 76.2% | 6.0% | 7.9% |
| 10 | 95.2% | 2.8% | 3.0% | 91.7% | 6.1% | 6.6% | 86.2% | 6.3% | 7.4% |
| 20 | 96.3% | 2.6% | 2.7% | 95.6% | 7.6% | 8.0% | 93.7% | 6.1% | 6.5% |
| 40 | 96.5% | 2.6% | 2.7% | 95.6% | 8.1% | 8.5% | 94.9% | 5.4% | 5.7% |
| 60 | 96.3% | 2.2% | 2.3% | 95.8% | 7.9% | 8.3% | 95.9% | 5.5% | 5.8% |

Figure 4:
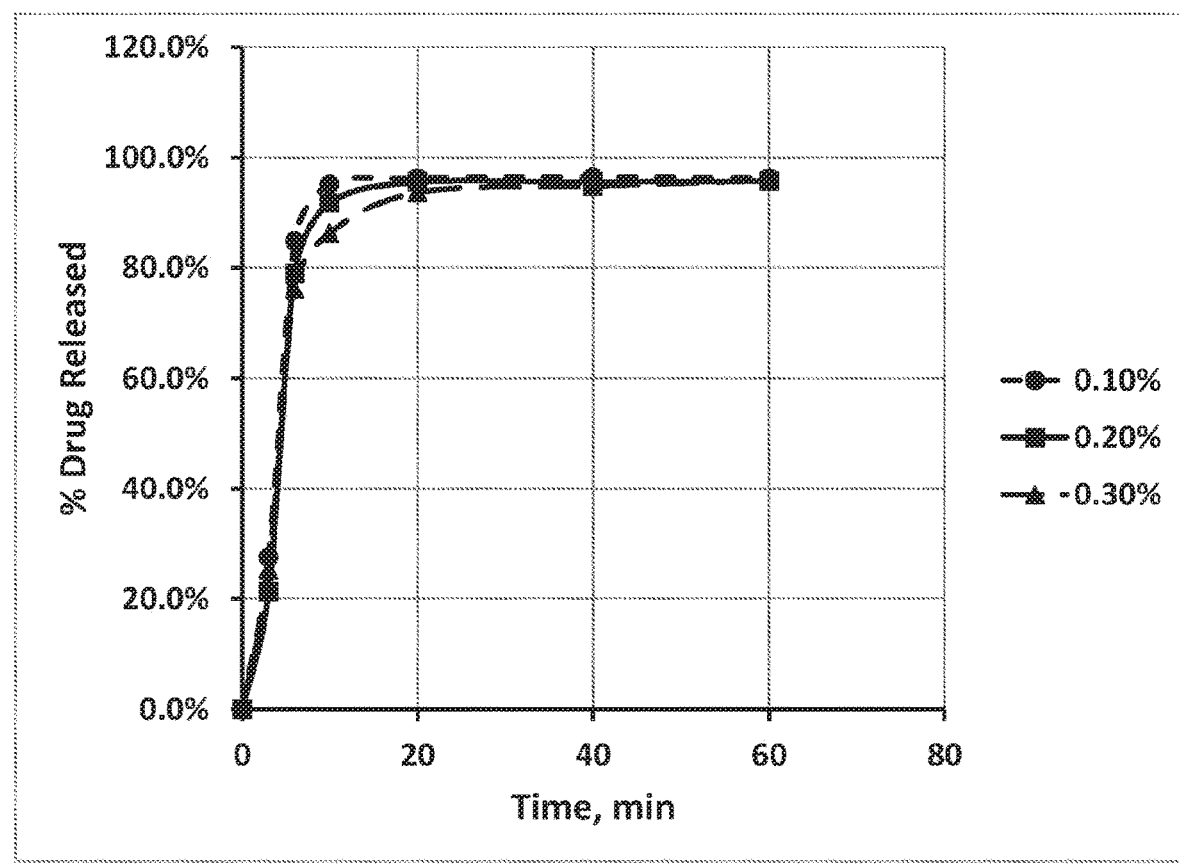
FIG. 4 shows the isotretinoin release profiles for three oral mucoadhesive films comprising 0.1% w/w, 0.2% w/w and 0.3% w/w isotretinoin.

Plots of drug dissolution profiles for Formulations L, M, and N are given in FIG. 4. All 3 formulations meet criterion of more than 85% drug release by end of dissolution (60 minutes). % RSD appears to be acceptable for all 3 formulations. Clear discriminations of drug dissolution profiles were showed among the 3 formulations of 0.1, 0.2, and 0.3% isotretinoin formulations.

EQUIVALENTS

The disclosure can be embodied in other specific forms with departing from the essential characteristics thereof. The foregoing embodiments therefore are to be considered illustrative rather than limiting on the disclosure described herein. The scope of the disclosure is indicated by the appended claims rather than by the foregoing description, and all changes that come within the meaning and range of equivalency of the claims are intended to be embraced therein.

What is claimed:

1. A method of treating an oral premalignant lesion in a patient in need thereof comprising applying to the oral premalignant lesion, for about 15 minutes to about 30 minutes once daily, an orally adhesive film comprising:
    a mucoadhesive layer comprising about 0.2 w/w % to about 0.3% w/w isotretinoin or a pharmaceutically acceptable salt thereof, about 11% to about 18% w/w vinylpyrrolidone-vinyl acetate co-polymer, and about 50% to about 60% polyvinylpyrrolidone (PVP); and
    an occlusive ingestible backing layer;
    thereby administering, by one directional release, an effective amount of the isotretinoin to the patient.

2. The method of claim 1, wherein the oral premalignant lesion is oral leukoplakia or oral erythroplakia.

3. The method of claim 1, wherein the PVP has a weight average molecular weight of about 70,000 g/mol to about 1,600,000 g/mol.

4. The method of claim 1, wherein the vinylpyrrolidone-vinyl acetate co-polymer has a weight average molecular weight of about 45,000 g/mol to about 70,000 g/mol.

5. The method of claim 1, wherein the mucoadhesive layer comprises about 0.3% w/w isotretinoin.

6. A method of treating an oral premalignant lesion in a patient in need thereof comprising mucosally applying to the oral premalignant lesion, once daily, an orally adhesive film comprising: a mucoadhesive layer comprising about 0.1% to about 0.3% w/w isotretinoin or a pharmaceutically acceptable salt thereof, about 12% w/w to about 15% w/w vinylpyrrolidone-vinyl acetate copolymer, about 53% w/w to about 57% w/w PVP, about 16% w/w to about 19% w/w PEG 400 and about 4% w/w to about 6% w/w propylene glycol; and an occlusive backing layer.

7. The method of claim 6, wherein the occlusive backing layer comprises poly(methacrylic acid-co-ethylacrylate) 1:1, poly(ethyl acrylate-co-methyl methacrylate-co-trimethyl-ammonioethyl methacrylate chloride) 1:2:0.2, and PEG 400.

* * * * *